United States Patent
Falco et al.

(10) Patent No.: US 7,464,786 B2
(45) Date of Patent: Dec. 16, 2008

(54) HIGH SOUND ATTENUATING HEARING PROTECTION DEVICE

(75) Inventors: Robert N. Falco, Indianapolis, IN (US); Richard Knauer, Carmel, IN (US); Alan R. Seville, Indianapolis, IN (US)

(73) Assignee: Cabot Safety Intermediate Corporation, Newark, DE (US)

( * ) Notice: Subject to any disclaimer, the term of this patent is extended or adjusted under 35 U.S.C. 154(b) by 237 days.

(21) Appl. No.: 10/866,212

(22) Filed: Jun. 11, 2004

(65) Prior Publication Data

US 2005/0274568 A1 Dec. 15, 2005

(51) Int. Cl.
*A61B 7/02* (2006.01)

(52) U.S. Cl. .................. 181/135; 181/129; 181/130; 181/136; D24/106; D24/173; D24/174

(58) Field of Classification Search ......... 181/128–130, 181/135–136; 128/864–867; D24/106, 173–174
See application file for complete search history.

(56) References Cited

U.S. PATENT DOCUMENTS

| | | | |
|---|---|---|---|
| 3,123,069 A | | 3/1964 | Laisne et al. |
| 4,314,553 A | * | 2/1982 | Westerdal .................. 128/864 |
| 4,434,794 A | * | 3/1984 | Leight ........................ 128/867 |
| 4,461,290 A | * | 7/1984 | Gardner et al. .............. 128/866 |
| 4,671,265 A | * | 6/1987 | Andersson ................... 128/866 |
| 4,819,624 A | * | 4/1989 | Leight et al. ................ 128/866 |
| 5,188,123 A | * | 2/1993 | Gardner, Jr. ................. 128/864 |
| 5,988,313 A | * | 11/1999 | Håkansson ................... 181/135 |
| 6,006,857 A | * | 12/1999 | Leight et al. ................ 128/864 |
| 6,241,041 B1 | * | 6/2001 | Leight ........................ 181/135 |
| 6,241,042 B1 | * | 6/2001 | Falco ......................... 181/135 |
| 6,393,130 B1 | * | 5/2002 | Stonikas et al. ............. 381/322 |
| 6,695,093 B1 | * | 2/2004 | Falco ......................... 181/135 |

FOREIGN PATENT DOCUMENTS

| | | |
|---|---|---|
| DE | 33 04 362 | 8/1984 |
| EP | 0 955 026 | 11/1999 |
| FR | 75 518 | 7/1961 |

OTHER PUBLICATIONS

Patent Cooperation Treaty; International Search Report; PCT/US2005/020858; Jun. 13, 2005.

* cited by examiner

*Primary Examiner*—Michale J Sherry
*Assistant Examiner*—Terrence R Willoughby
(74) *Attorney, Agent, or Firm*—Cantor Colburn LLP

(57) ABSTRACT

A hearing protection device insertable into an ear canal is provided, the device generally including a stem portion, a sound attenuating portion affixed to and extending at least partially over the stem portion, and a volume of space disposed between and delimited by the sound attenuating portion and the stem portion, where at least a part of the sound attenuating portion is collapsible into the volume of space during insertion of the hearing protection device into the ear canal.

60 Claims, 19 Drawing Sheets

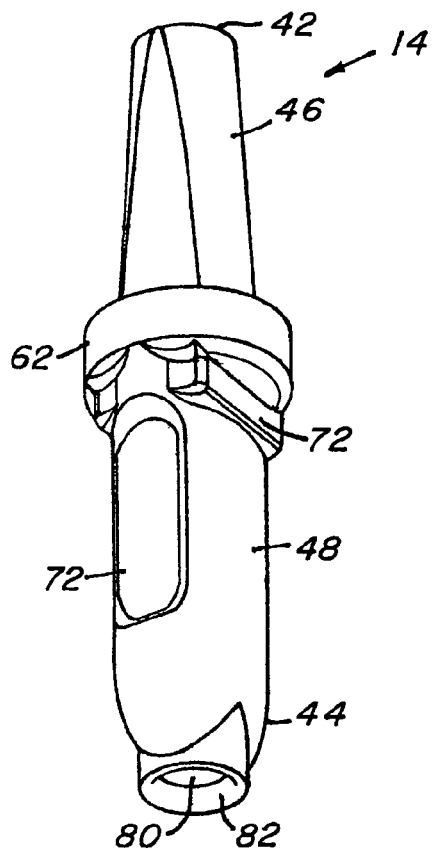
FIG. 8
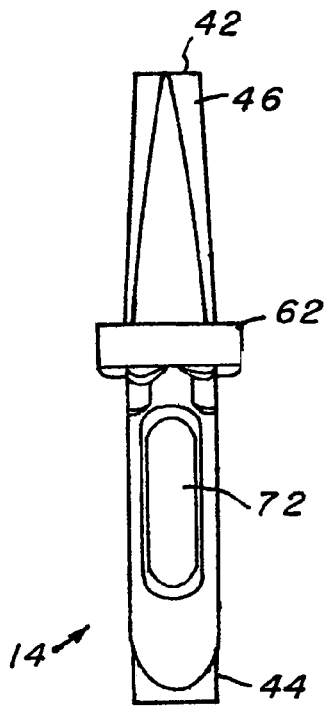
FIG. 9
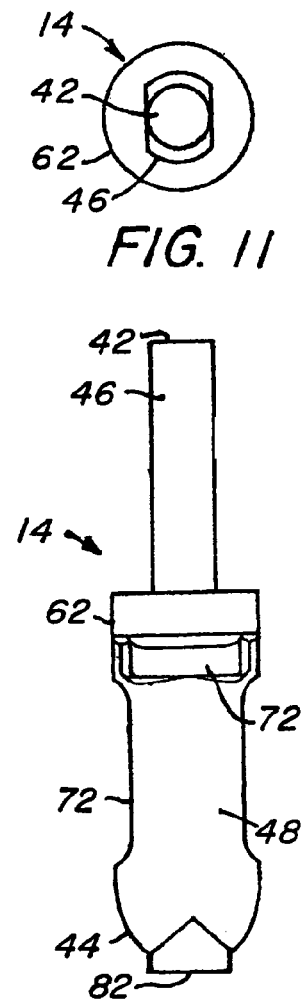
FIG. 10
FIG. 11
FIG. 12

HIGH SOUND ATTENUATING HEARING PROTECTION DEVICE

TECHNICAL FIELD OF INVENTION

The invention generally concerns hearing protection devices and, more particularly, an earplug insertable into an ear canal which provides a high sound attenuation.

DESCRIPTION OF RELATED ART

Hearing protection devices, such as earplugs, are readily used to provide sound attenuation. Earplugs include any of a variety of devices designed to be inserted in the ear canal of a user and worn therein to prevent sounds from entering.

Push-in type earplugs generally comprise an attenuating portion and a rigid or semi-rigid portion typically extending therefrom or embedded therein. The sound attenuating portion is typically of a soft compressible material; the rigid or semi-rigid portion may be composed of any material, such as a plastic or a rubber, with sufficient rigidity as required.

To insert the push-in type earplug, the user grasps the rigid/semi-rigid portion (or an end of the earplug proximate thereto), positions the earplug proximate the ear canal opening, and inserts the sound attenuating portion into the canal by pushing with the rigid/semi-rigid portion. The sound attenuating portion compresses, as necessary, upon entry into the ear canal and is held therein by a friction fit, occluding the canal and providing sound attenuation.

Such a push-in type earplug may be found, for example, in U.S. Pat. Nos. 4,867,149 and 5,188,123 to Falco and Gardner Jr., respectively, which are herein incorporated by reference in their entirety.

These known push-in type earplugs have been found to be effective at attenuating sound and thus providing sufficient hearing protection to the wearer. For example, such earplugs, when properly inserted have been shown to provide a Noise Reduction Rating (hereinafter, "NRR") of approximately 25 dB. However, often a relatively higher level of sound attenuation is desired. For example, an earplug wearer in a particularly high-sound environment may desire an NRR of approximately 30 dB or higher.

This heightened sound attenuation is known to be provided by foam roll-down type earplugs, such as that disclosed by U.S. Pat. No. 6,105,715 to Knauer, which is herein incorporated by reference in its entirety. However, the high performance of these roll-down earplugs is directly dependent upon proper insertion and fit thereof. See, e.g., Laboratory Attenuation of Earmuffs and Earplugs Both Singly and in Combination, Am. Ind. Hyg. J. 44(5), 321-329 (1983).

As with push-in type earplugs, roll-down plugs attenuate sound by causing an occlusion deep within the ear canal, thus obstructing the passage of sound therethrough. However, the required insertion method is slightly more complex, requiring a precise roll-down of the plug and a manipulation of the pinna portion of the ear during ear canal insertion. See, U.S. patent application Ser. No. 10/740,180 filed on Dec. 17, 2003, which is herein incorporated by reference in its entirety.

Errors during insertion of roll-down earplugs result in improper fit within the ear canal, and thus full occlusion may not be achieved. For example, the earplug may be rolled down properly, but only inserted partially into the ear canal. Thus, the surface area of the plug in contact with the ear canal walls is reduced, full occlusion is not attained, and attenuation is degraded. Further, the earplug may be mis-handled during pre-insertion roll-down preparations. For example, the plug may improperly rolled and/or compressed prior to insertion such that creases are formed on the surface of the plug. These creases act as sound channels and permit the leakage of sound into the canal, thus degrading occlusion, and effecting attenuation.

Push-in type earplugs are considered by many to provide easier insertion than other types of plugs. As discussed above, the wearer simply grasps the rigid or semi-rigid portion (or the end of the earplug proximate thereto) and inserts the sound attenuating portion at the opposite end into the ear canal, lodging the earplug therein and, hence, occluding the canal.

However, while allowing a simplistic insertion, the push-in type earplug typically does not yield the higher attenuations often provided by roll-down type earplugs. This may be because the push-in plug typically has a lesser surface area contacting the ear canal when inserted therein, or perhaps because the push-in plug wrinkles or folds during insertion creating leaks, or, further, because the push-in plug does not stay firmly in place during use and backs slightly out of the ear canal.

Accordingly, a hearing protection device is desired which is inserted simply and effectively, which stays firmly in place in the ear canal after insertion during usage, which is comfortable to the user, and which provides a relatively high sound attenuation.

BRIEF SUMMARY OF THE INVENTION

The above discussed and other problems and deficiencies of the prior art are overcome or alleviated by the invention which provides a novel and nonobvious hearing protection device.

As set forth herein, a hearing protection device insertable into an ear canal is provided, the device generally including a stem portion, a sound attenuating portion affixed to and extending at least partially over the stem portion, and a volume of space disposed between and delimited by the sound attenuating portion and the stem portion, where at least a part of the sound attenuating portion is collapsible into the volume of space during insertion of the hearing protection device into the ear canal. Also, a sound attenuating portion for use in such device is specifically provided as set forth herein.

BRIEF DESCRIPTION OF THE DRAWINGS

Referring now to the drawings wherein like elements are numbered alike in the several FIGURES:

FIG. 8 is a perspective view of an earplug stem in one embodiment of the invention;

FIG. 9 is a side view of the stem of FIG. 8;

FIG. 10 is another side view of the stem of FIG. 8;

FIG. 11 is a front view of the stem of FIG. 8;

FIG. 12 is a rear view of the stem of FIG. 12;

DETAILED DESCRIPTION OF THE INVENTION

Figure 1:
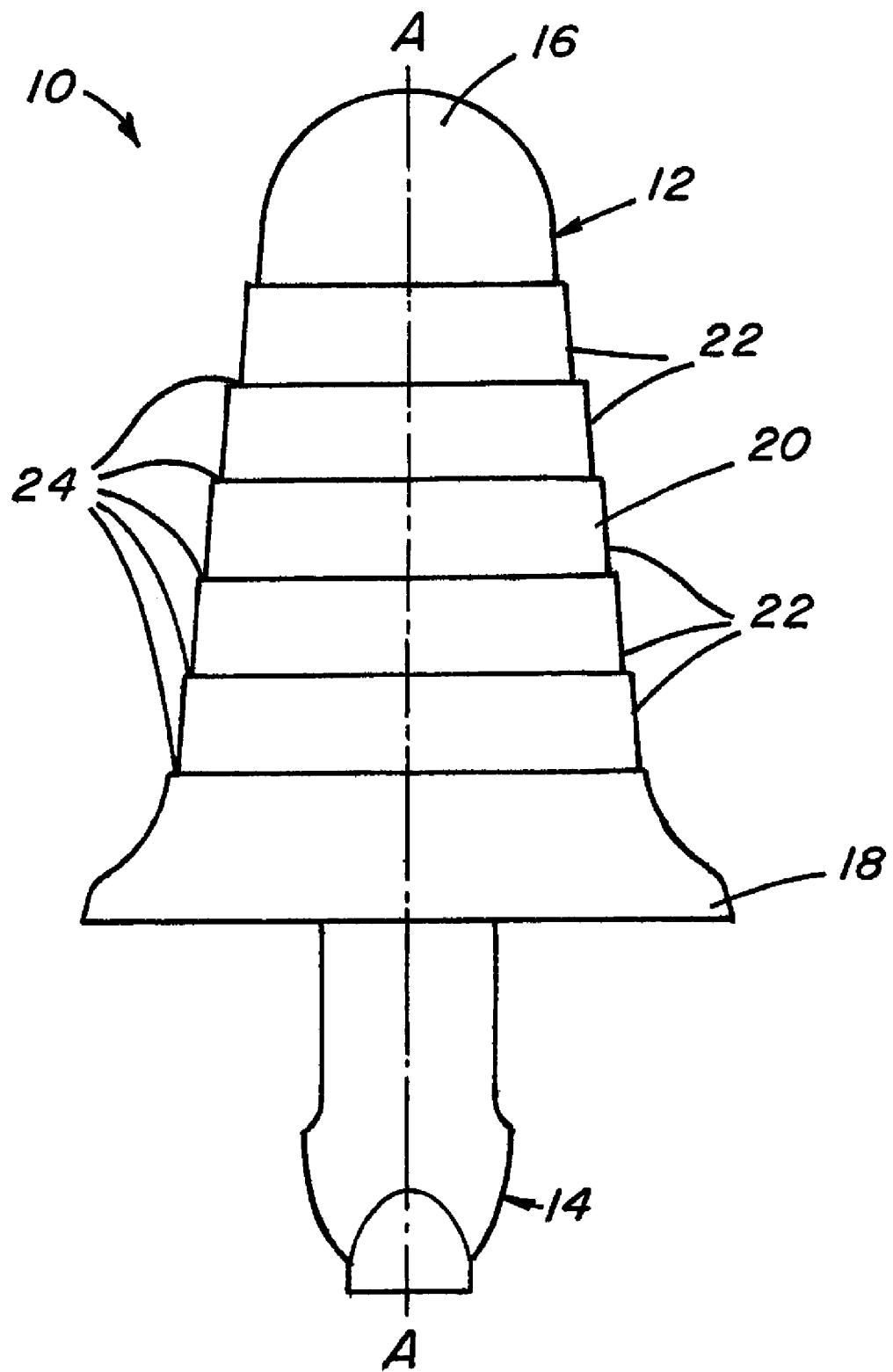
FIG. 1 is a side elevational view of an earplug in one embodiment of the invention.
Figure 2:
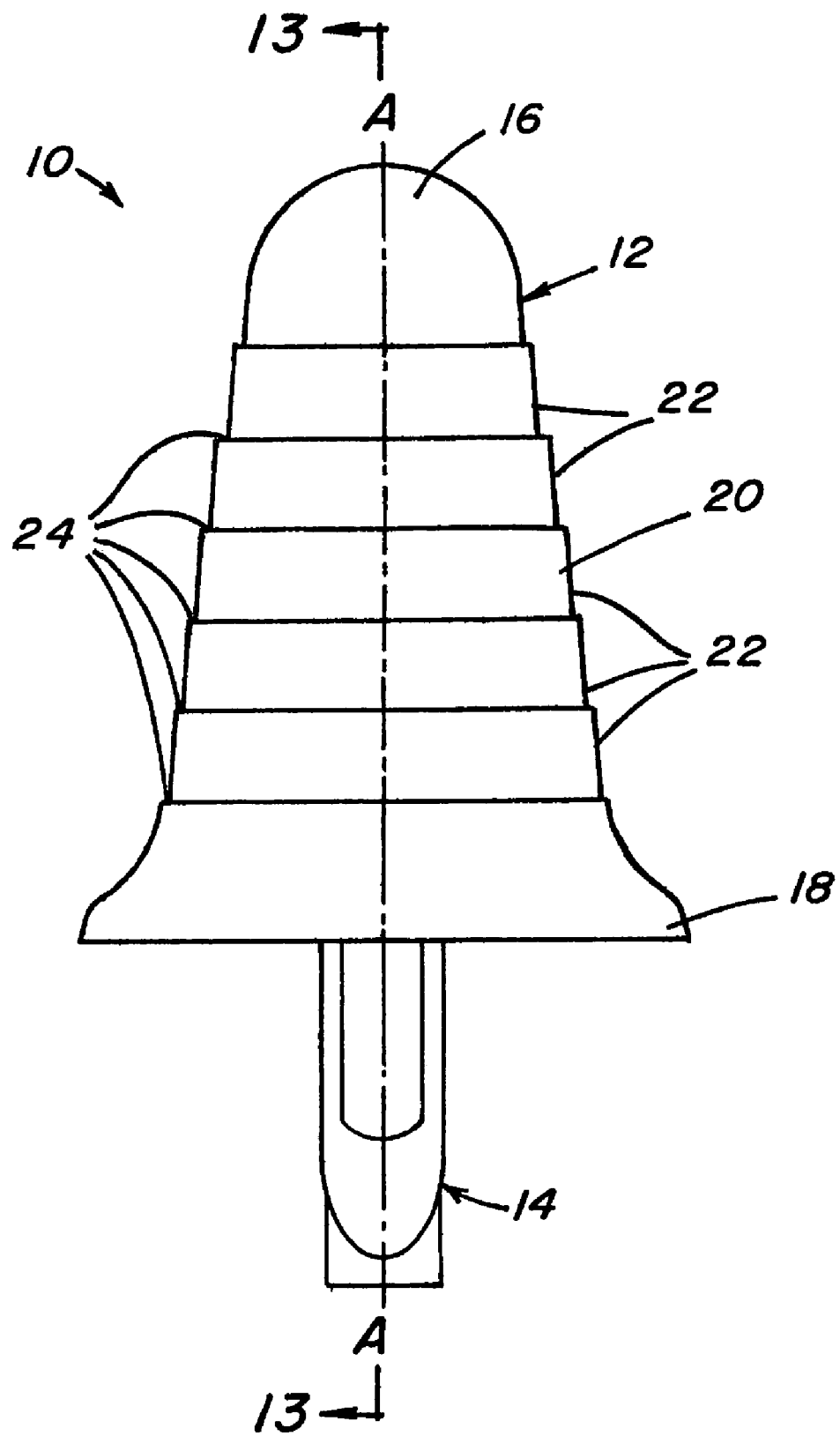
FIG. 2 is another side elevational view of the earplug of FIG. 1.

FIGS. 1-5 show various views of an earplug 10 in one exemplary embodiment of the invention. The earplug 10 generally comprises a sound attenuating portion 12 and a stem portion 14 attached to the sound attenuating portion 12 and extending rearwardly therefrom. The attenuating portion 12 is composed of a sufficiently soft material and is generally shaped and configured to be readily inserted into an ear canal, to be comfortably retained therein, and to provide an enhanced level of sound attenuation, all of which will be further discussed herein. The stem portion 14 is formed of a rigid or semi-rigid material and is generally configured to facilitate handling of the earplug 10 and to facilitate a simple ear canal insertion and removal thereof, all of which are further discussed herein.

Herein, the term 'front' and 'frontwardly' will be used to indicate a position on or about the described earplugs proximate to an end of the earplug which enters the ear canal first when the earplug is properly inserted. 'Rear' and 'rearwardly' shall herein indicate a position on or about the described earplugs opposite that designated by 'front' and 'frontwardly'.

Turning first to the sound attenuating portion 12, a bulbous portion 16 is provided at a front insertion end of the earplug 10. In a preferred embodiment, the bulbous portion 16 is substantially hemispherical in shape. Alternatively, however, the bulbous portion 16 may be partially hemispherical, partially spherical, cylindrical, rectilinear, or may be a solid formed of a parabolic or hyperbolic curve, or, more generally, the bulbous portion 16 may be any desired shape which is suitable for facilitating insertion of the earplug 10 into an ear canal.

The sound attenuating portion 12 includes a flared portion 18 disposed opposite the bulbous portion 16. The flared portion 18 essentially comprises a rim at the rear end of the sound attenuating element 12 which extends outwardly from a longitudinal axis A-A of the earplug 10. Preferably, the flared portion 18 follows a smooth curvilinear path from a body portion 20 of the earplug 10 outwardly from the axis A-A to the rearmost end of the sound attenuation portion 12 where the flared portion 18 terminates. In alternative embodiments of the invention, the flared portion 18 may comprise a straight-line path originating at the body portion 20 and angling outward from the body portion 20 away from the axis A-A to a point of terminus. Of course, the flared portion 18 may include a profile which is partially curvilinear in nature and partially straight-line, as desired. More generally, the flared portion comprises a rim at the rear end of the sound attenuating portion 12, the rim having any desirable shape so as to extend at least partially outward from the longitudinal axis A-A of the earplug 10 and at least partially rearward with respect to the plug 10.

The body portion 20 extends between the bulbous portion 16 and the flared portion 18 of the sound attenuating portion 12. The body portion 20 generally tapers from the flared portion 18 towards the bulbous portion 16 and includes a generally circular cross-section such that a diameter thereof taken proximate to the flared portion 18 is larger than a diameter taken proximate the bulbous portion 16. That is, the body portion 20 is substantially frustoconical in shape having a narrow end meeting the bulbous portion 16 and a wider base end terminating at the flared portion 18.

In a preferred embodiment, the outer surface of the body portion 20 comprises a plurality of rings 22 arranged side-by-side, extending from the bulbous portion 16 to the flared portion 18, the rings 22 having serially increasing diameters. The rings 22 are essentially a plurality of longitudinally extending, cylindrical bands having different diameters formed on the outer surface of the body 20. The arrangement of the rings 22 across the surface of the body portion 20 forms a plurality of corresponding steps 24. That is, the rings 22 give the body portion 20 a stepped profile. (See, e.g., FIG. 1.) Each step 24 comprises a rim or ridge formed on a frontward edge of the respective ring 22, the rim traversing around the body portion 20 and extending outward (with respect to the axis A-A) from the next forwardly disposed ring 22.

Figure 3:
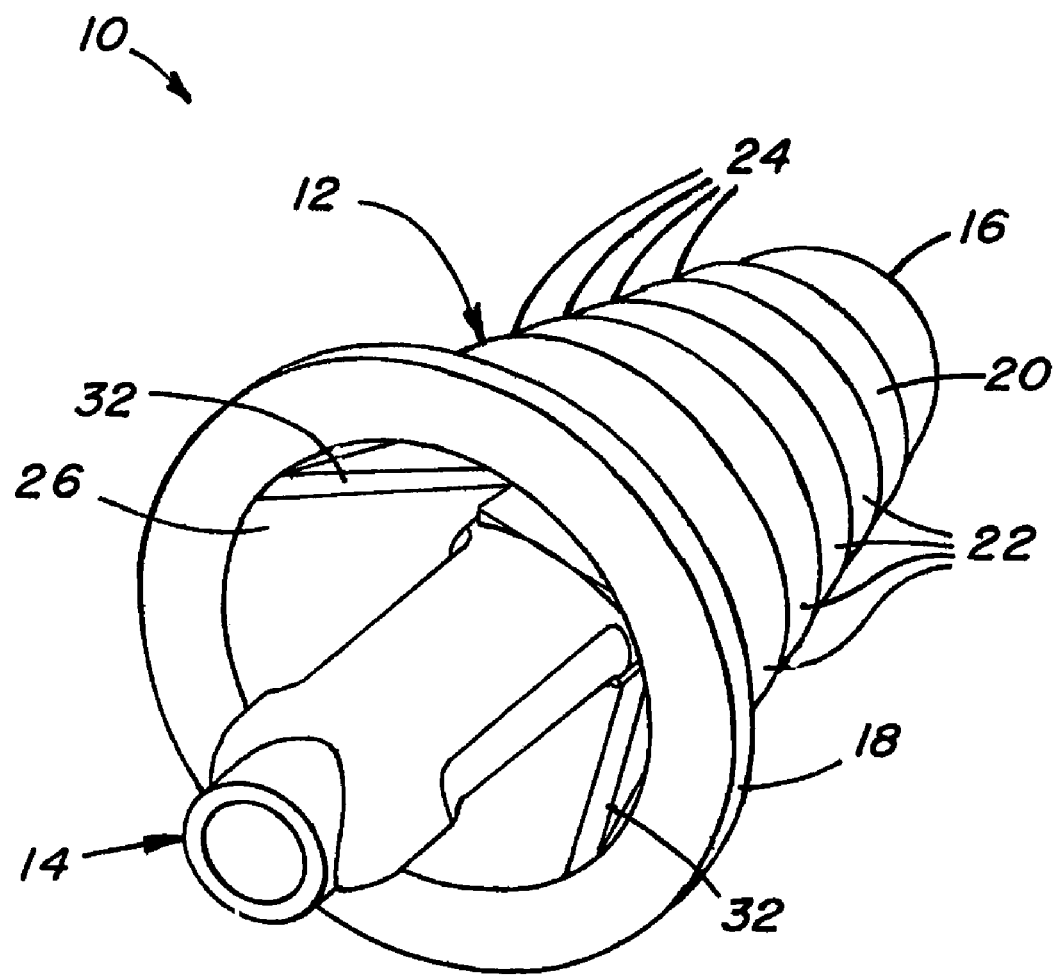
FIG. 3 is a rear perspective view of the earplug of FIG. 1.
Figure 4:
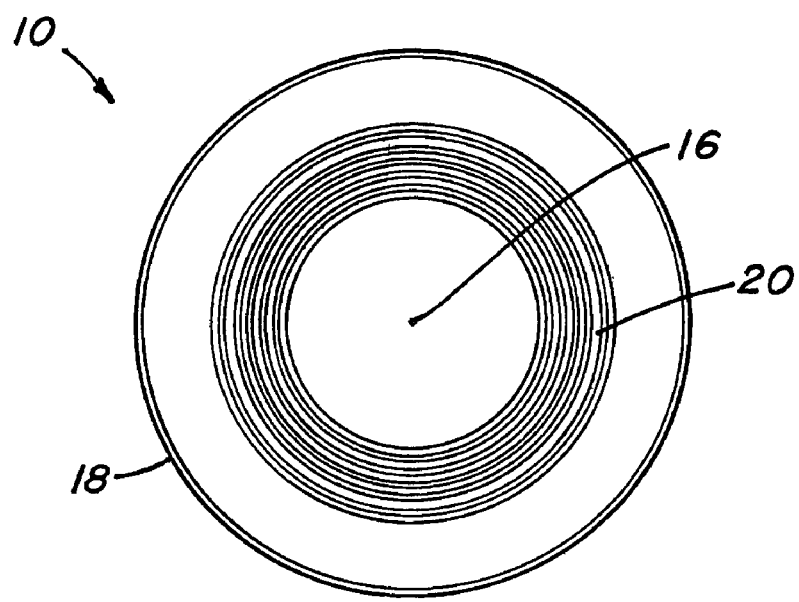
FIG. 4 is a front view of the earplug of FIG. 1.
Figure 5:
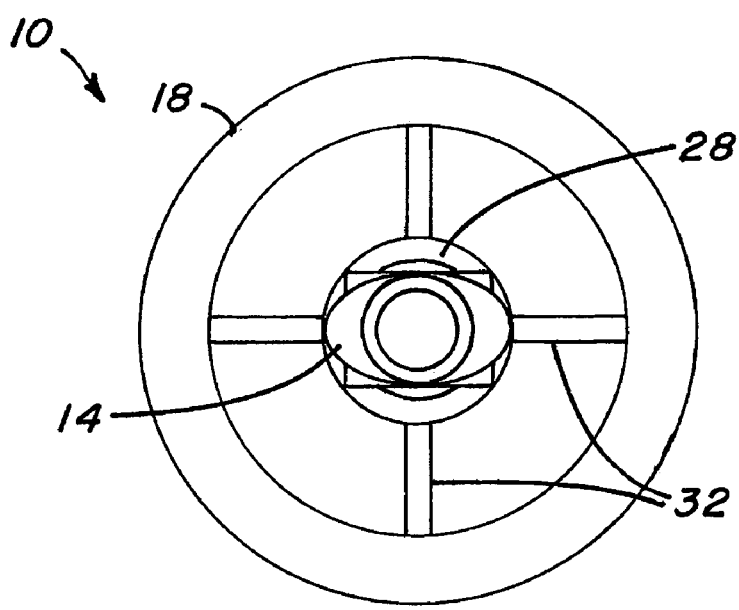
FIG. 5 is a rear view of the earplug of FIG. 1.

A rear view of the earplug 10, as provided in FIGS. 3 and 5, reveals that the sound attenuating element 12 includes a hollow interior 26 delimited by the body portion 20 and the flared portion 18. That is, the body portion 20 includes thin walls which form its outer, above-discussed, frustoconical shape and which delimit the hollow interior 26. As shown, the flared portion 18 is annular in shape and forms an opening of the interior 26 at a rear of the sound attenuating element 12. In a preferred embodiment, the hollow interior 26 is partially frustoconical in shape as best seen in the cross-sectional view of FIG. 13. Of course, the inner surfaces of the walls forming the body portion 20 may have any shape or contoured to thus shape the interior 26 as desired. For example, the walls of the body portion 20 may be configured such that the interior is substantially cylindrical, or partially cylindrical, partially spherical, or generally rectilinear or curvilinear, or any combination of these or other shapes.

Figure 6:
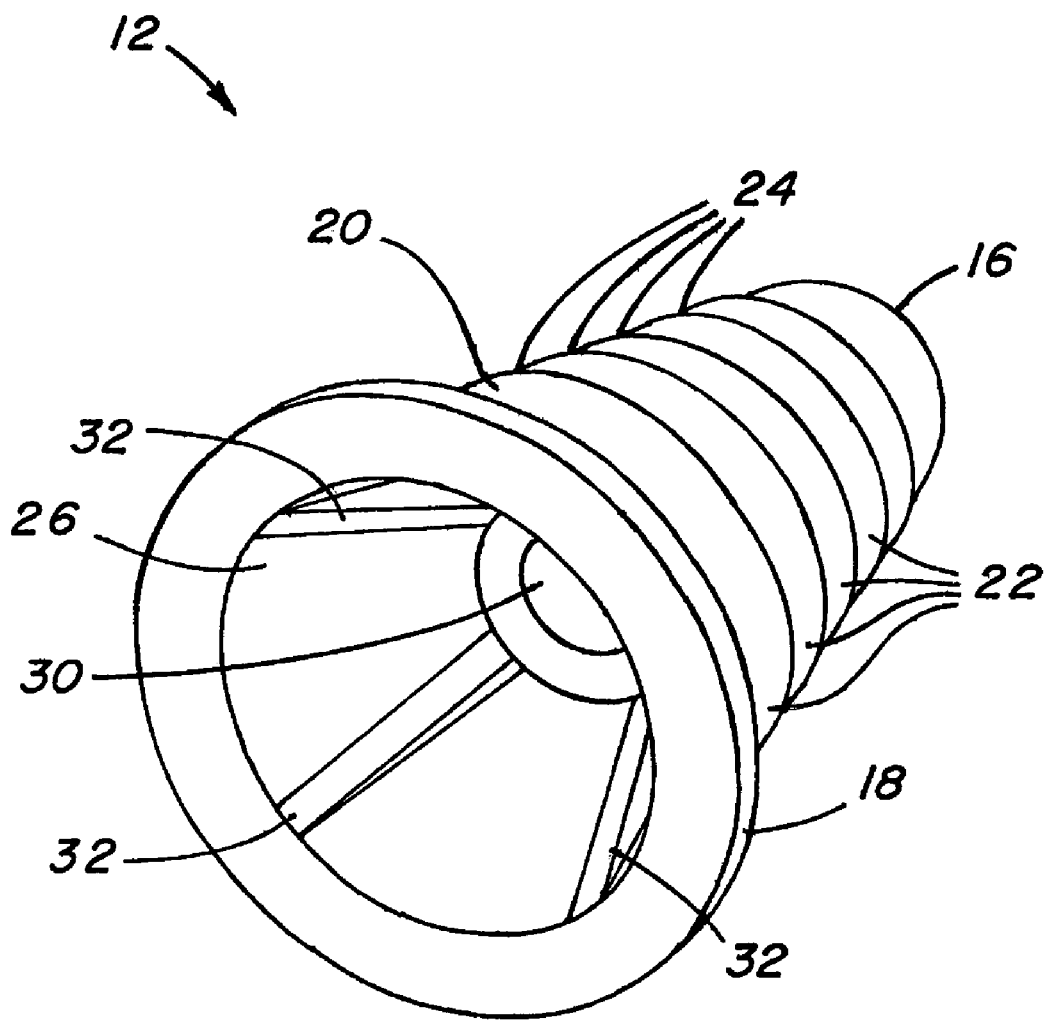
FIG. 6 is a rear perspective view of a sound attenuating portion of the earplug of FIG. 1.
Figure 7:
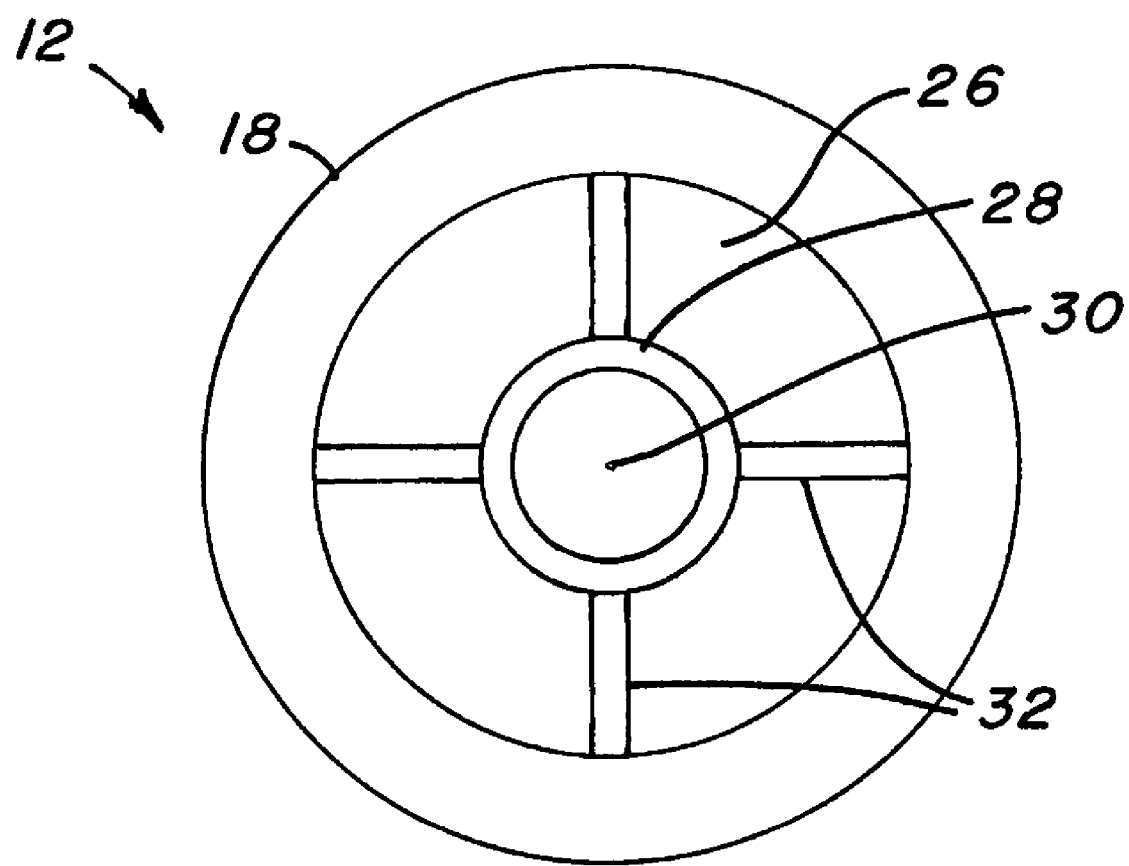
FIG. 7 is a rear view of the sound attenuating portion of FIG. 6.
Figure 13:
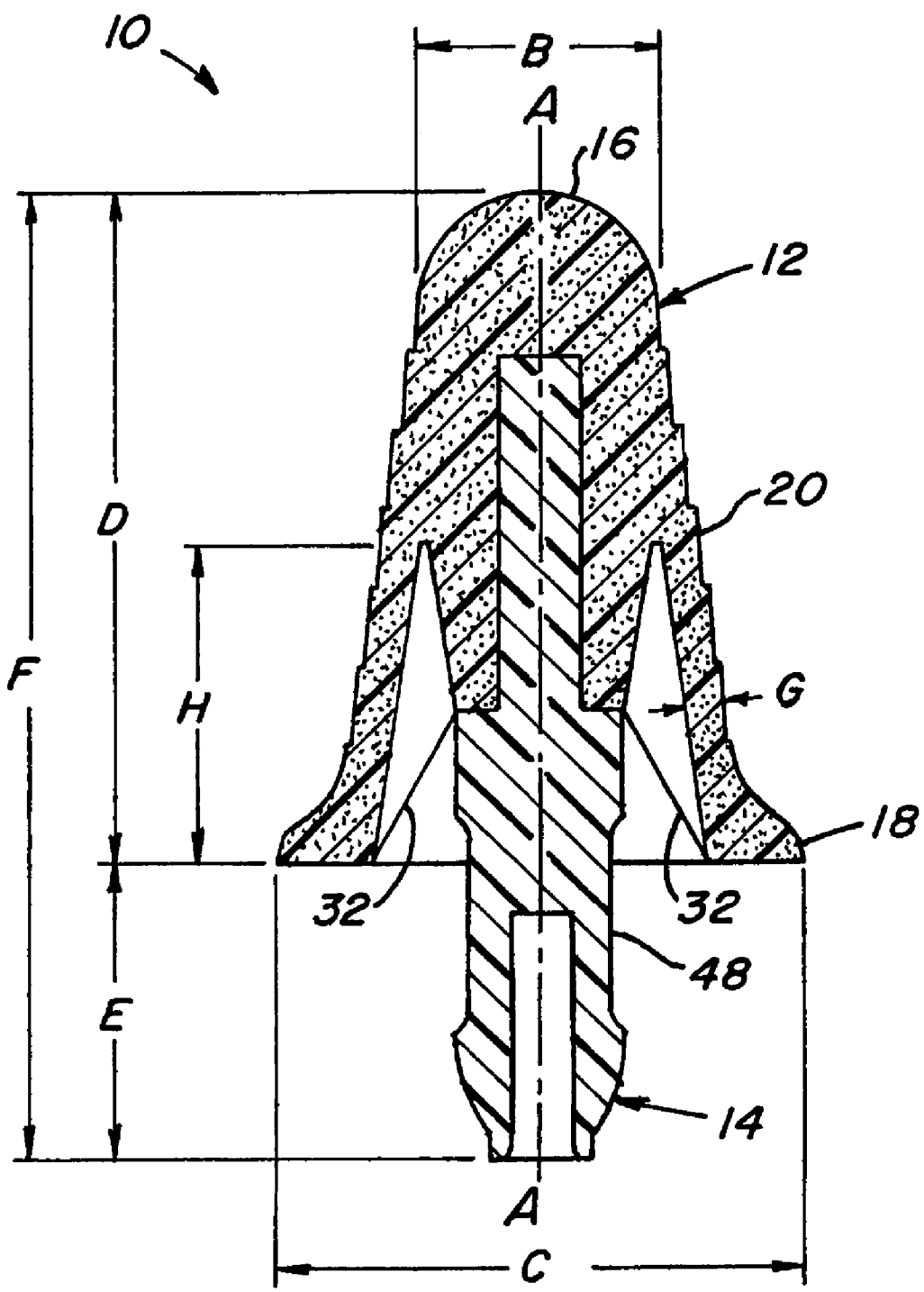
FIG. 13 is a cross-section view of the earplug of FIG. 2 taken along line A-A of FIG. 2.

The sound attenuating element 12 includes a sleeve 28 formed at the interior 26 extending from the element 12 in a rearward direction along the axis A-A of the earplug 10, as best shown in FIGS. 6 and 13. The sleeve 28, in a preferred embodiment, is a hollow cylindrical form with a rearwardly disposed open end. The sleeve 28 at least partially delimits a cavity 30 which extends toward the bulbous portion 16 of the sound attenuating element 12 along the axis A-A thereof.

The sleeve 28 and the corresponding cavity 30 are particularly configured for receiving and retaining the stem portion 14. That is, the stem portion 14 seats within the sleeve 28 at the cavity 30 and is fixed therein to the sound attenuating portion 12. The sleeve 28 is preferably composed of the same material as the sound attenuating portion 12 is formed integrally therewith. The cavity 30 extends through the sleeve and may extend beyond the sleeve 28 toward the bulbous portion 16. That is, in one embodiment, the cavity 30 extends into the body portion 20 beyond a frontward limit of the interior 26 of the sound attenuating element 12 and terminates approximately at the rearward end of the bulbous portion 14.

The cavity 30 is generally cylindrical in shape and may taper slightly toward the bulbous portion 16 such that a cross-section of the cavity 30 taken proximate the bulbous portion 12 is smaller than a section taken at the sleeve 28. More generally, both the sleeve 28 and the cavity 30 may include any shape and/or configuration suitable for receiving the stem portion 14 and facilitating retention thereof.

The sound attenuating element 12 further includes a plurality of ribs 32 formed on the body portion 20 at the interior 26. Preferably, the ribs 32 each extend along the inner surface of the body portion 20, generally from the flared portion 18 frontwardly toward the bulbous portion 16. The ribs 32 terminate frontwardly at a region of the interior 26 where the sleeve 28 meets the body portion 20. Towards this region, the ribs 32 are attached to both the inner surface of the body portion 20 and the sleeve 28.

In an exemplary embodiment, the ribs 32 are each substantially shaped as an inclined plane which inclines toward the front of the earplug 10 as seen in the Figures. That is, the ribs 32 include a rectilinear cross-section having a gradually increasing cross-sectional area in a direction toward the front of the earplug 10 such that a cross-sectional area of a rib 32 taken proximate the sleeve, for example, is larger than an area thereof taken proximate the flared portion 18. Similarly, however, the ribs 32 may comprise a curvilinear cross-section or a cross-section having both curvilinear and rectilinear features. While the gradually increasing cross-sectional area of the ribs 32 is preferred, the invention contemplates ribs having a uniform or variable cross-section, as desired.

As mentioned, the sound attenuating portion 12 includes a plurality of ribs 32. Preferably, four ribs 32 are disposed on the body portion 20 at the interior 26 and are equally spaced thereon, i.e., rear ends of the ribs 32 as disposed proximate to the flared portion 18 are spaced apart at substantially 90°. The sound attenuating portion 12 may include more or fewer ribs 32, of course, as desired.

In a general sense, the stem portion 14 of the invention comprises a rigid or semi-rigid element affixed to or disposed within the sound attenuating portion 12 for facilitating handling of the earplug 10 and insertion and removal thereof with respect to an ear canal. For example, the stem portion 14 may comprise a stem as described in U.S. patent application Ser. No. 10/236,595 filed on Sep. 6, 2002 by Taylor and assigned to the Assignee of the present application, which application is herein incorporated by reference in its entirety. However, the stem portion 14 may herein comprise a more general element as that shown in FIGS. 15-16.

The preferred embodiment of the stem portion 14, as best shown in FIGS. 8-12 includes a front stem end 42 and an opposing rear stem end 44. An inserted portion 46 is formed at the front stem end 42 and a handle portion 48 is formed at the rear stem end 44. The inserted portion 46 is intended to be inserted in, received by, and retained within the sleeve 28 of the sound attenuating portion 20. The handle portion 48 is disposed so as to extend at least partially from the sound attenuating portion 20 to facilitate handling of the earplug 10 and insertion and removal thereof with respect to an ear canal.

The inserted portion 46 is generally a cylindrical element and, in one embodiment, includes a generally circular cross-sectional area which tapers in a direction toward the front stem end 42, i.e., the circular cross-sectional area is larger proximate the rear stem end 44 and gradually becomes smaller along a length of the inserted portion 46 in a direction toward the front stem end 42. The invention generally contemplates the inserted portion having any desired cross-section (e.g., circular, oval, generally curvilinear, square, rectangular, generally rectilinear, or any combination or modification thereof) suitable for being received within the sleeve 28 and being retained therein to the sound attenuating portion 20 of the earplug 10.

The handle portion 48, in a preferred embodiment as shown in FIGS. 8-12, extends from the rear stem end 44 in a direction toward the front stem end 42 and meets the inserted portion 46 at a point approximately midway between the front and rear stem ends 42 and 44. The handle portion 48 includes a collar 62 proximate the inserted portion 46. The collar 62 is a generally cylindrical element having a cross-sectional area greater than the cross-sectional areas of the inserted and handle portions 46 and 48, i.e., the collar circumferentially extends beyond a remaining section of the handle portion 48 as well as beyond the inserted portion 46 such that the stem 14 has a largest cross-sectional area at the collar 62.

The handle portion 48 is generally cylindrical in cross-section, as shown in the Figures, but may include any desired cross-sectional shape including curvilinear or rectilinear shapes, or any combination and/or modification thereof. The handle 48 in this exemplary embodiment further includes features 72 formed on an outer surface thereof. The features 72 may comprise recesses or projections, or combinations thereof, formed on an outer surface of the handle portion 48 for facilitating the handling of the stem 14 and/or for providing an area to dispose indicia such as graphics, brand names, logos, etc.

The handle portion 48 of the stem 14 further includes a cavity 80 formed at an interior of the handle portion 48. See, FIGS. 8 and 13. The cavity 80 is exposed to an exterior of the stem 14 at an opening 82 formed at the rear stem end 44. The cavity 80 extends axially along a length of the handle portion 48 in a direction toward the front stem end 44. in one embodiment, the cavity 80 terminates at a point approximately midway between the rear stem end 44 and the collar 44. The cavity 80 has a substantially circular cross-section which, in one embodiment tapers slightly in a direction toward the collar 62, i.e., the cross-sectional area of the cavity 80 gradually. reduces over the length of the cavity in a direction from the rear stem end 44 toward the collar 62. The cavity 80 and the opening 82 are particularly designed to receive and retain an earplug cord 100 as shown, for example, in FIG. 14.

Figure 15:
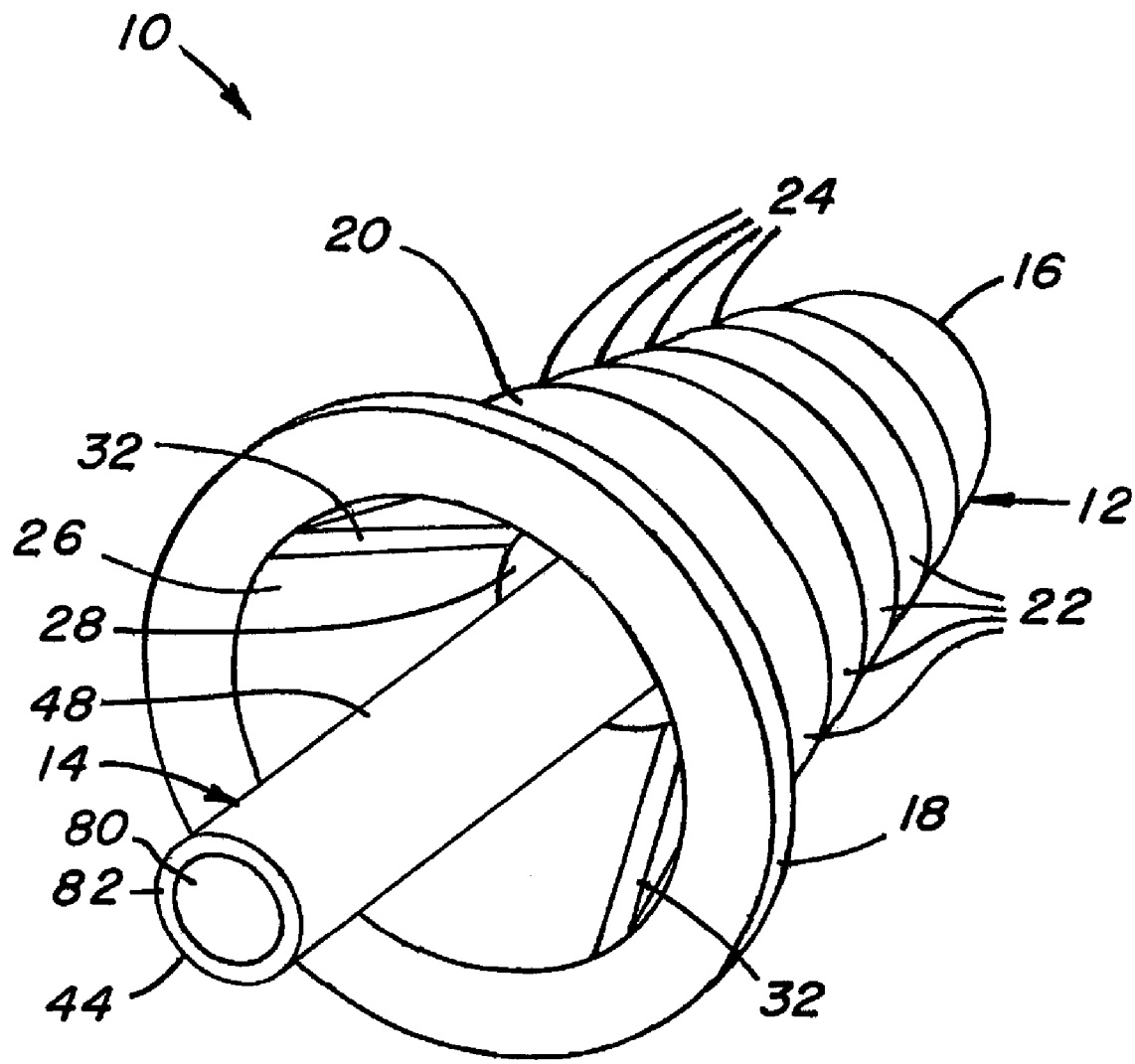
FIG. 15 is a rear perspective view of an earplug in another embodiment of the invention.
Figure 16:
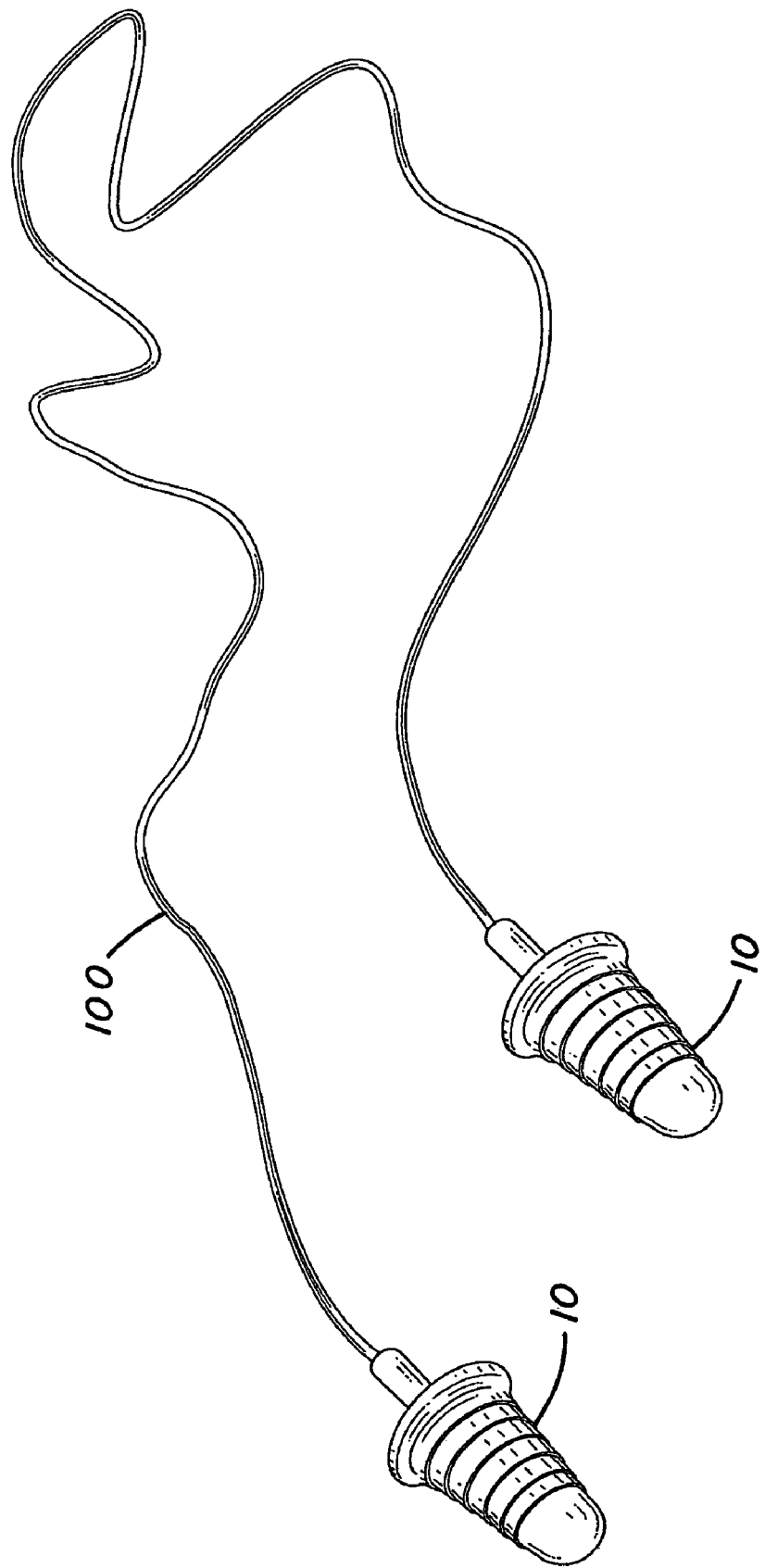
FIG. 16 is a perspective view of a pair of earplugs according to FIG. 15 attached by a cord.

As mentioned, the stem shown in detail in FIGS. 8-12 represents a mere preferred embodiment. Alternatively, the stem 14 may comprise a simple cylindrical element as shown in FIGS. 15-16 including the above-discussed front and rear stem ends 44 and 46, respectively, the inserted portion 46, the handle portion 48, etc. Here, however, the handle portion 48 is a simple cylindrical shape and may additionally include, as desired, tapering our contouring to facilitate handling of the earplug 10, receipt and retention of the stem 14 in the sleeve 28, etc.

In sum, the stem portion 14 of the invention is a rigid or semi-rigid element affixed to the sound attenuating portion 20 and extending therefrom for facilitating handling of the earplug 10, where the stem includes any desired shape or additional gripping features, tapering, and/or contouring as desired.

Figure 14:
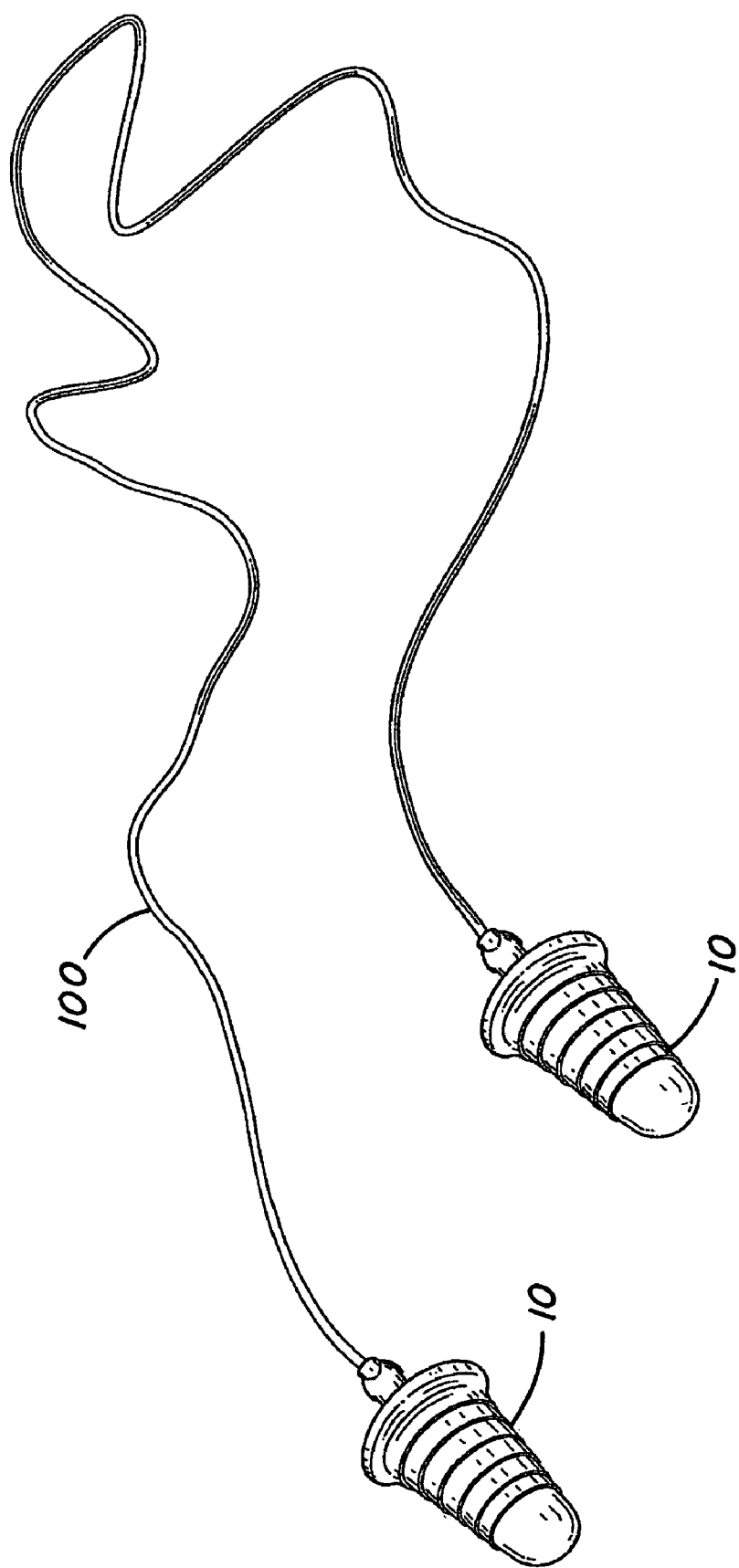
FIG. 14 is a perspective view of a pair of earplugs according to FIG. 1 attached by a cord.

FIG. 14 shows a pair of the earplugs 10 of FIG. 1 attached by a cord 100. The cord is received through the opening 82 and in the cavity 80 of the stem portions 14 of each of the earplugs 10. See FIGS. 8-12 and related description. FIG. 16 shows the cord 100 similarly attached to a pair of the earplugs 10 of FIG. 15. In both examples, the cord 100 is retained within the respective stem portions 14 by any sufficient retention means such as, for example, by friction fit, adhesive bonding, chemical or mechanical bonding, thermal welding, molding processes, etc. Here, the earplugs 10 are inserted as described above and the cord 100 may be optionally worn behind the neck or under the chin and presents a convenient means for handling and suspending the earplugs and for generally keeping two earplugs together and associated with one another.

Generally, the earplug 10 as disclosed herein may be sized as desired to provide a comfortable and reliable fit to the wearer and to yield and high sound attenuation. The dimensions for one preferred embodiment of the earplug 10 shall now be discussed with particular reference to FIG. 13. A cross-sectional diameter B of the bulbous portion 16 is approximately 0.250-0.500 inches, and is preferably approximately 0.312 inches. A cross-sectional diameter of the flared portion 18 is approximately 0.500-0.750 inches, and is preferably approximately 0.653 inches. A longitudinal length D of the sound attenuating portion 20 is approximately 0.750-1.250 inches, and is preferably approximately 0.882 inches. A longitudinal length E of a portion of the stem 14 extending rearwardly beyond the flared portion 18 is approximately 0.250-0.500 inches, and is preferably approximately 0.375 inches. Thus an overall longitudinal length F of the earplug 10 is approximately 1.0-1.75 inches, and is preferably approximately 1.257 inches. A thickness G of the freely extending walls of the body portion 20 is approximately 0.05-0.07 inches and may be consistent or variable over a length H of the walls. The length H is the length of the body portion 20 which extends freely from the plug 10, i.e., which extends over the interior 26. The length H is approximately 0.70-1.00 inches, and is more preferably approximately 0.89 inches.

It shall be understood that the above-described dimensions are merely exemplary and that the earplug of the invention may comprise any desired dimensions suitable for facilitating insertion of the earplug 10 in the ear canal and for providing a enhanced sound attenuation.

Figure 20:
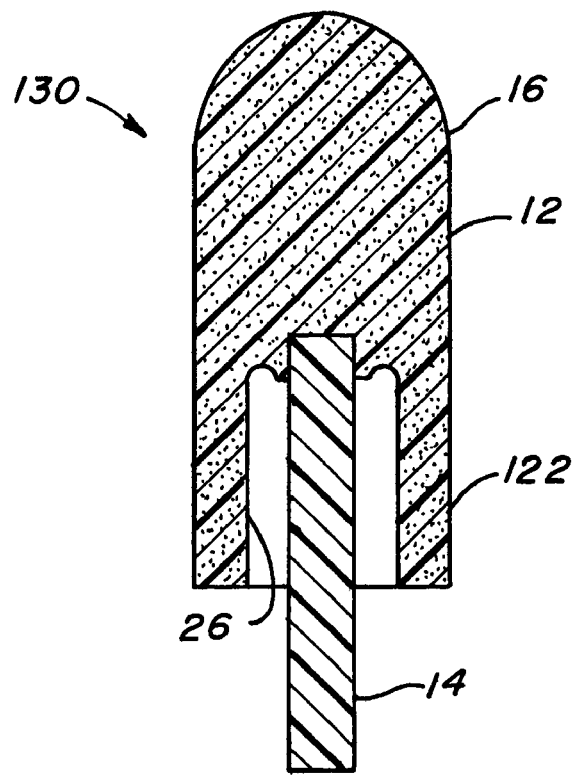
Figure 21:
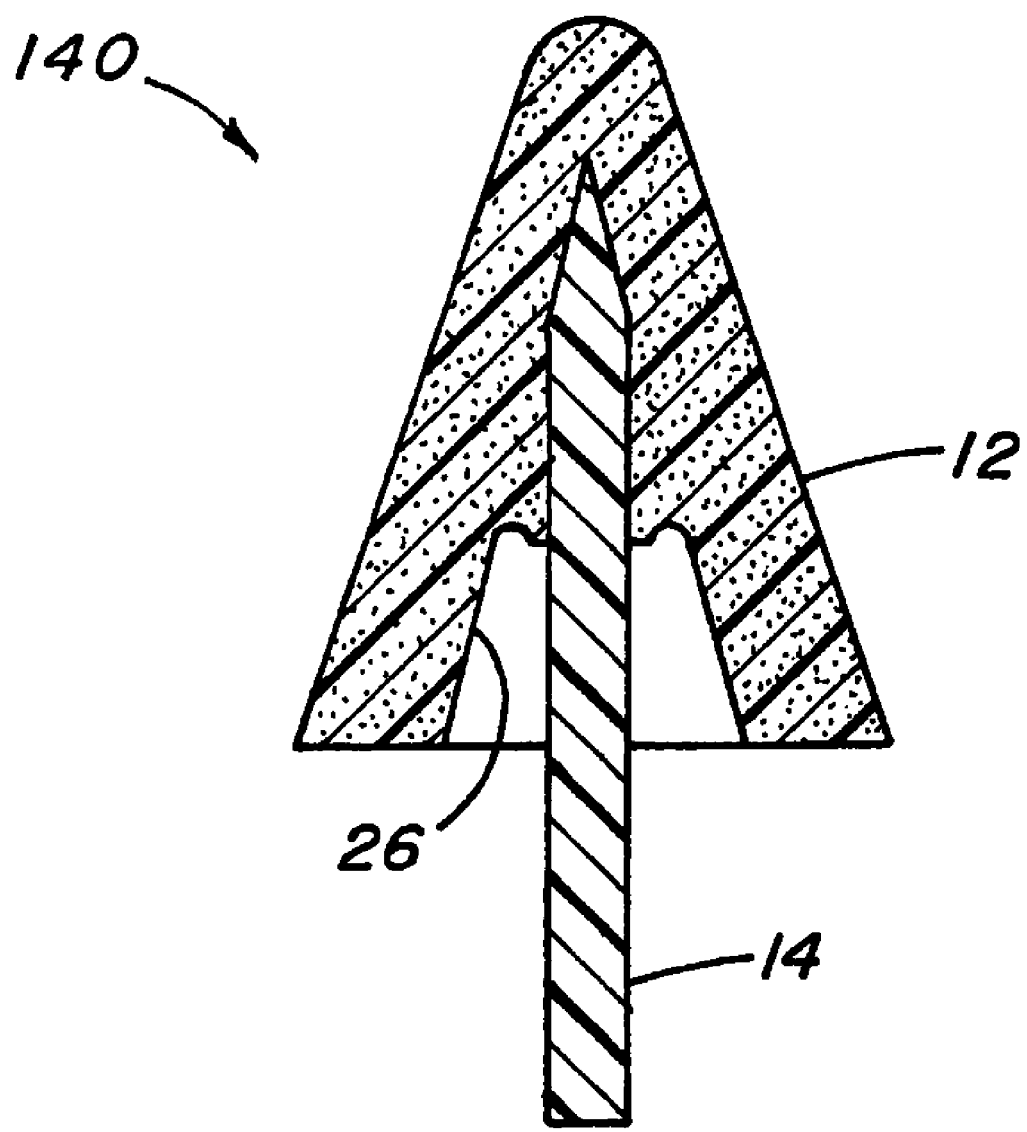
Figure 29:
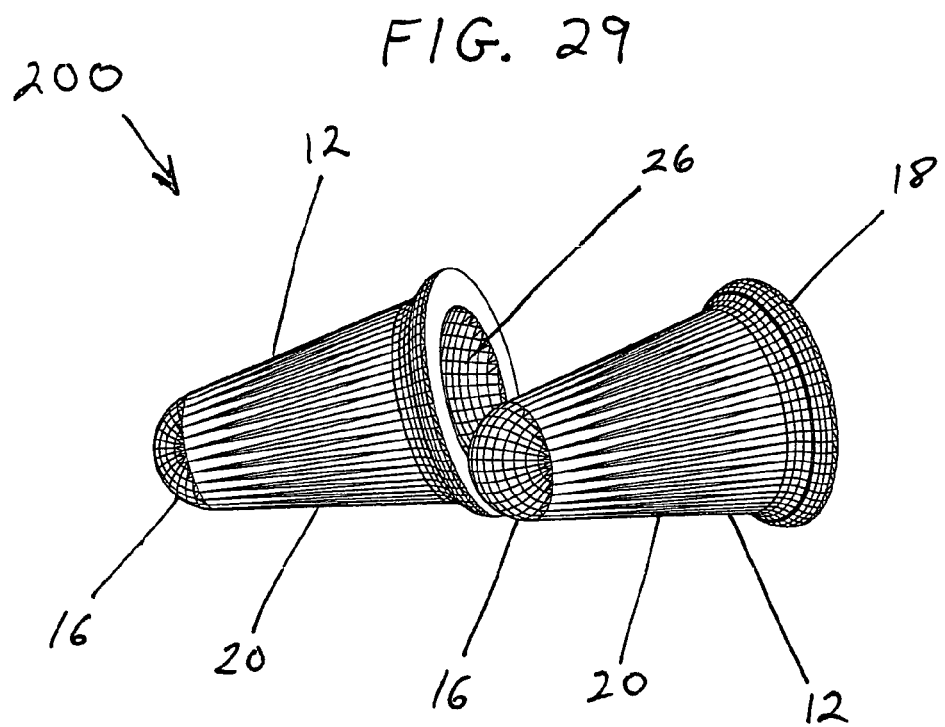
FIG. 29 is a perspective view of a pair of earplugs in an additional embodiment of the invention.
Figure 30:
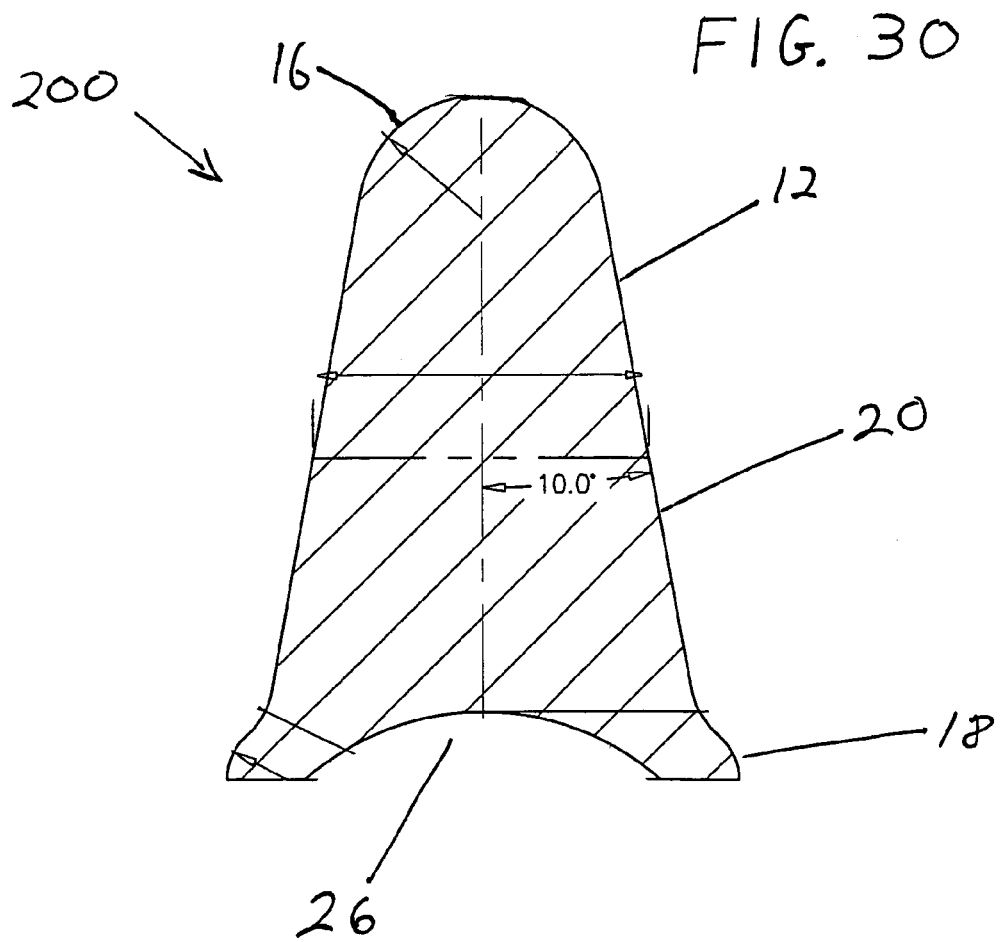
FIG. 30 is a cross-sectional view of an earplug of FIG. 29.

For example, the dimension H, which defines the length of the body portion 20 extending freely from the plug 10 and over the interior 26, may be configured as to define a deeper or shallower interior 26. The exemplary embodiment of FIG. 13 discussed above, shows an interior 26 length H that is approximately half the longitudinal length D of the sound attenuating portion 20. FIG. 20 shows a similar configuration to FIG. 13 with regard to the length of the interior 26 relative to the longitudinal length of the sound attenuation portion 12. In comparison, FIGS. 17-19 and 22-25 illustrate an interior 26 length that is approximately proportionally greater than half of the longitudinal length of the sound attenuation portion 12, thus defining a longer or deeper interior 26. On the other hand, the exemplary embodiments of FIGS. 21, 29, and 30 show an interior 26 having a length that is proportionally approximately less than half of the longitudinal length of the sound attenuating portion 12, thus defining a shorter or more shallow interior 26.

The sound attenuating portion 12 of the earplug 10 is made, preferably, of a compressible resilient material such as, for example, a compressible resilient plastic or rubber material or composition. Preferably, the sound attenuating portion 12 is composed of a foam-like material composed of a soft, pliable self-rising foam with slower recovery properties such as a polyurethane or an acrylic blend foam. Other suitable foams include PVC, silicone, and nitrile, among others. A suitable foam is described, for example, in U.S. Pat. No. 5,792,998 to Gardner, Jr. et al., herein incorporated by reference. The earplug described therein is comprised of a dynamically stiff foam material having a low static stiffness, and a high dynamic stiffness. Another suitable foam is described, for example, in U.S. Pat. No. 4,158,087 to Wood, herein incorporated by reference in its entirety. In a preferred exemplary embodiment, a polyurethane foam is used to form the sound attenuating element 12 where the foam measures a Shore OO durometer of approximately 20 to 40, and preferably approximately 30. However, as mentioned, the sound attenuating portion 12 may be formed of any suitable compressibly resilient material such as plastics including thermoplastic elastomers, etc.

The stem portion 14 of the earplug 10 is made of any suitable pliable, semi-rigid, or rigid material as is desired. Particularly, the stem member 14 may be composed of a plastic or a rubber material and may be formed, preferably, by injection molding. The material forming the stem portion 14 includes a Shore A durometer of approximately 60-100, and more preferably approximately 80.

The earplug 10 is manufactured, in one embodiment, by first forming the sound attenuating portion 12 and the stem portion 14, and then adhesively bonding the inserted portion 46 of the stem portion 14 to the sound attenuating portion 12 at the sleeve 28. Alternatively, the sound attenuating portion 12 may be formed about the stem portion 14 such that the sleeve 28 mechanically or chemically bonds to the inserted portion 46. For example, a foam material forming the attenuating portion 12 may be formed around an end of the stem such that the foam bonds directly to the stem due to a chemical affinity between the two materials. Of course, the invention contemplates other conventional methods of manufacture which suitably lead to the production of the earplug 10.

In use, the earplug 10 is handled by the stem portion 14 at the handle 46 and brought proximate the ear of a user. Then, the bulbous portion 16 of the sound attenuating element 12 is inserted into the opening of the ear canal and inserted into the canal by pushing on the rear end 44 of the stem portion 14. The sound attenuating element 12 compresses within in the ear canal and lodges therein to attenuate the passage of sound from the outer environment to the inner ear. The handle 46 of the stem 14 remains at or extends from the ear canal when the earplug 10 is fully inserted. To remove the earplug 10, the user grasps the exposed stem portion 14 and pulls the earplug 20 from the ear canal.

As the earplug 10 enters the ear canal during insertion, the material forming the sound attenuating portion 12 compresses, as mentioned above. Particularly, the bulbous portion 16 and the portion of the body 20 proximate thereto compress inward toward the axis A-A and slightly rearward. Additionally, the forces exerted on the earplug 10 during ear canal insertion cause the freely extending portion of the body 20 to collapse slightly into the hollow interior space 26.

Due to features of the earplug 10 described hereinabove, the plug 10 generally reacts oppositely to these insertion forces. For example, the material used to form the sound attenuating portion 12, when compressed during insertion, exerts an oppositely directed resilient force tending to expand the sound attenuating portion 12 to its non-compressed state. The cantilevered construction of the extending portion of the sound attenuating body 20 also reacts oppositely to the compressive insertion forces and the ribs 32 further add to the resiliency of the sound attenuating portion 12.

This combination of a very soft and compressible, yet resilient sound attenuating portion 12 contributes to the earplug 10's enhanced occlusion of the ear canal and its resulting high attenuation. That is, when the earplug 10 is inserted, the sound attenuating portion 12 is compressed and forms to the shape of the ear canal. The hollow interior 26 allows the extending body portion 20 to collapse therein as necessary to completely conform to the shape and contours of the ear canal. Yet, the resilient features of the sound attenuating portion 12 maintain full contact of the outer surface of the sound attenuating portion 12 with the skin forming the ear canal, providing full occlusion of the ear canal and keeping the earplug 10 snugly lodged therein during use. This full occlusion thus results in a relatively high sound attenuation.

The flared portion 18 of the sound attenuating portion 20 further contributes to the effectiveness of the earplug 10. The flared portion 18 extends outwardly from the longitudinal axis A-A of the earplug 10 to seal the rear of the earplug 10 around the inner surface of the ear canal. That is, the extension of the flared portion 18 contacts the skin of the ear canal continuously, thus providing full occlusion of the canal even if the body portion 20 is wrinkled or otherwise for some reason not making full contact with the ear canal.

The stem portion 14 also contributes to the occluding effectiveness of the earplug 10. The semi-rigidity provided by the stem portion 14 enables the user to quickly and easily insert the earplug 10 to a preferred depth within the ear canal, thus ensuring full contact of the entire outer surface of the sound attenuating portion 12 with the skin forming the ear canal and, correspondingly, providing maximum occlusion. Yet, the stem portion 14 is still pliable enough to bend slightly during insertion and use of the earplug 10 to conform generally to the shape and contours of the ear canal, thus providing comfort to the user and facilitating retention of the earplug 10 within the canal even during vigorous use. Also, it is noted that the stem portion 14 provides the earplug 10 with a core of material of different type and of higher density than that forming the sound attenuating portion 12. These multiple materials forming the earplug 10 and their varying densities further serve to enhance the sound attenuation provided thereby. Finally, the contouring and grip features of the stem portion 14 as shown in FIGS. 8-12 facilitate the user's handling of the earplug 10 and aid the easy ear canal insertion thereof.

The rings 22 and resulting steps 24 formed on the outer surface of the sound attenuating portion 12 further contribute to the overall effectiveness of the earplug 10 as a sound attenuator. First, the rings 22 essentially form ridges which are gently pressed into the skin of the ear canal during use to prevent unwanted slipping or moving of the inserted earplug 10. Additionally, the frontwardly decreasing diameter of the rings 22 give the body portion 20 of the earplug 10 a tapered profile which eases insertion thereof and ensures maximum surface contact of the sound attenuating portion 12 with the skin of the ear canal. Additionally, it is noted that the rings 22 and corresponding steps 24 provide a gripping feature of the earplug 10 which facilitates handling thereof by the user prior to and after insertion.

As described at length herein, the sound attenuating portion 12, in a preferred embodiment, is substantially frustoconical in shape. Also as described herein, the hollow interior 26 extends beneath at least the flared portion 18 and the body portion 20 of the sound attenuating portion 12, thus giving the portion 12 an essentially elongated bell-shape. See, e.g., FIGS. 1, 3, and 13. That is, the earplug 10 generally comprises one elongated flange element (the sound attenuating portion 12, particularly the body and flared portions 18, 20) extending rearwardly over the stem member 14. This elongated flange element accounts for approximately 50-80% of the longitudinal length of the earplug 10 and, more preferably, accounts for approximately 70% of the length of the plug 10. The elongated flange element is collapsible into the hollow interior 26 disposed thereunder. That is, the freely extending part of the body portion 20 and the flared portion 18 is pivotal relative to the longitudinal axis A-A of the earplug 10. Thus, upon ear canal insertion, not only does the material composing the sound attenuating portion 12 compress and conform to the shape and size of the ear canal, but the body and flared portions 18, 20 also fully collapse into the hollow interior 26 as necessary to further configure the earplug 10 to the dimensions of the ear canal, thus providing enhanced occlusion thereof and maximum sound attenuation.

Figure 17:
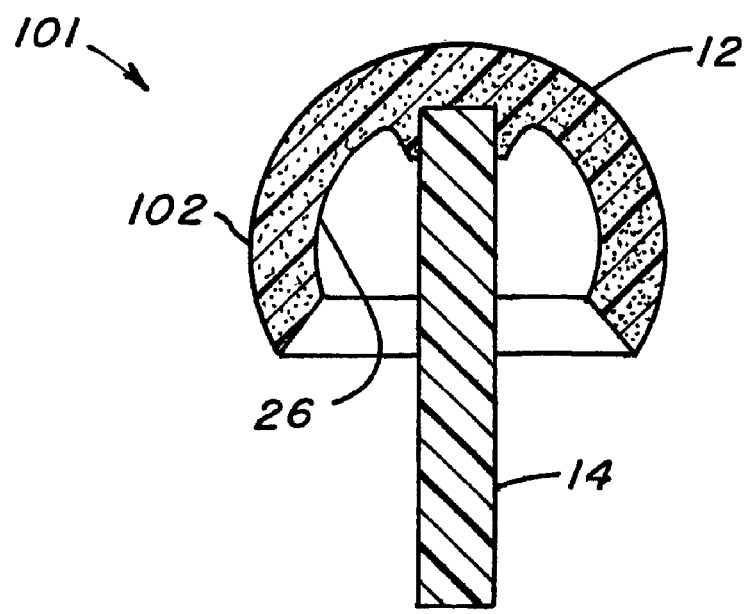
FIGS. 17-28 are cross-sectional views of the earplug in additional embodiments of the invention.
Figure 18:
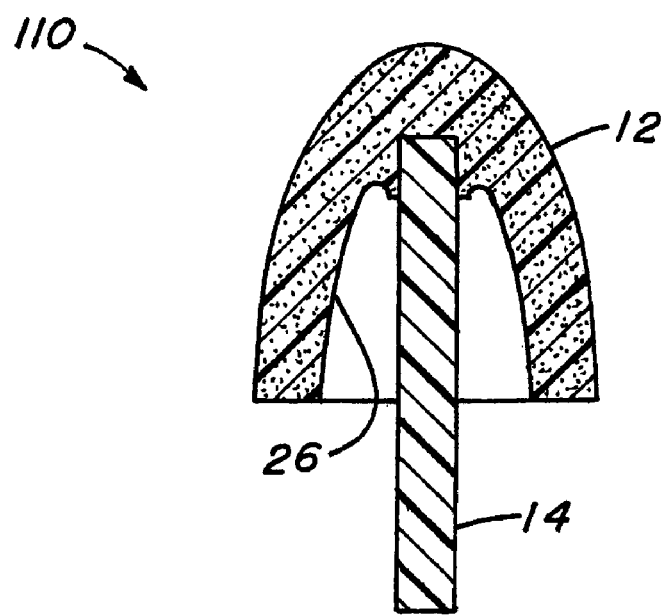
Figure 19:
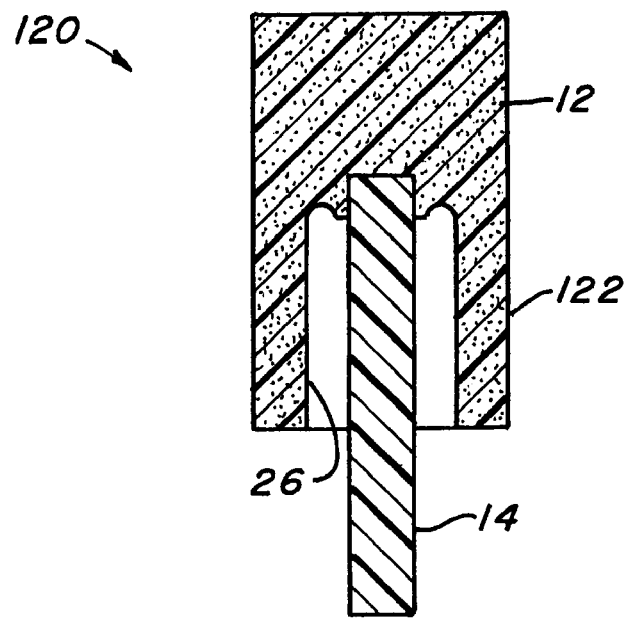

While the sound attenuating portion 12 has been generally described thus far as including a frustoconical "bell-shape", the invention contemplates the attenuating portion 12 including generally any shape having at least a part thereof extending over the stem 14 and over the hollow interior 26 to form a single rearwardly extending collapsible flange. FIGS. 17-21 show alternate embodiments of the earplug of the invention. Like parts are indicated with consistent reference numerals herein throughout. FIG. 17 shows a cross-sectional view of an earplug 101 having the sound attenuating 12 and the rearwardly extending stem portion 14. Here, however, the sound attenuating portion 12 is shaped partially spherical and includes a freely extending rearwardly directed portion 102 which is collapsible into the hollow interior 26 upon insertion of the plug 100 into the ear canal. Preferably, the flange 12 of FIG. 17 includes a partially spherical shape greater than hemispherical but less than fully spherical. In FIG. 18 shows an earplug 110 in section including a sound attenuating portion 12 having a partially oval or parabolically-formed shape extending rearwardly over the stem 14 and collapsible into the hollow interior 26. An earplug 120, as shown in cross-section in FIG. 19, includes a cylindrical shaped sound attenuating portion 12 including a rearwardly extending part 122 which is collapsible into the hollow interior 26, as necessary, during insertion and use thereof. Earplug 130 of FIG. 20 is also substantially cylindrical in shape but includes the bulbous portion 16 described herein above. The sound attenuating portion 12 of the earplug 130 is collapsible into the hollow space 26 upon ear canal insertion, as necessary. An earplug 140 is shown in FIG. 21 as including a generally conical sound attenuating portion 20, also collapsible into the hollow interior 26 thereof. These and other shapes and collapsible configurations of the sound attenuating portion are contemplated by and are within the scope of the hearing protection device of the invention.

While the stem portion 14 has thus far been described as a generally straight, elongated element as shown in FIGS. 1, 2, 3, 5, and 8-21, the invention contemplates the stem portion 14 as including generally any shape or contouring as desired to facilitate insertion, retention, and removal of the earplug 10 relative to the ear canal.

Figure 22:
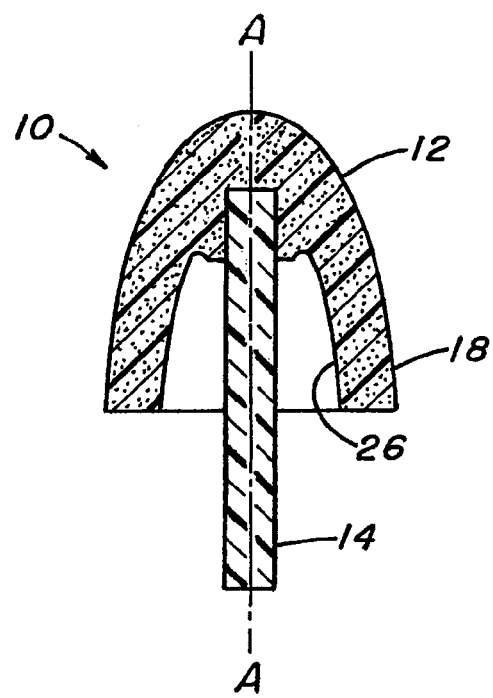

That is, as shown in FIG. 22, the stem portion 14 has generally been described herein to include an elongated cylindrical element extending rearwardly from the sound attenuating portion 12 along the longitudinal axis A-A of the earplug 10. The stem portion 14 is centered within the circumference formed by the flared portion 18 as the stem 14 extends from the attenuation portion 12.

Figure 23:
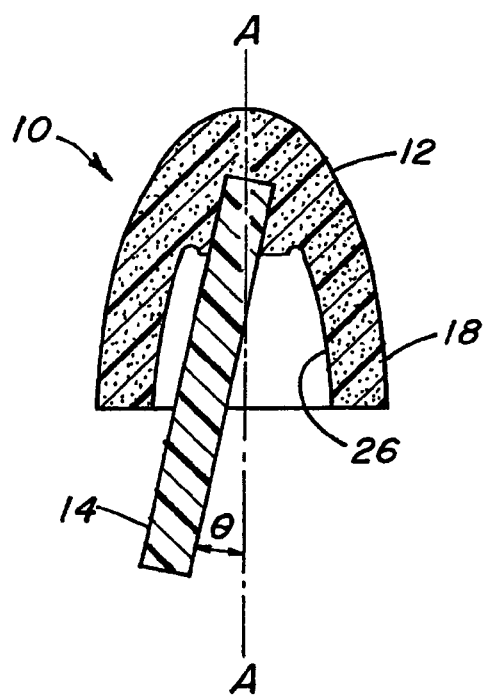
Figure 24:
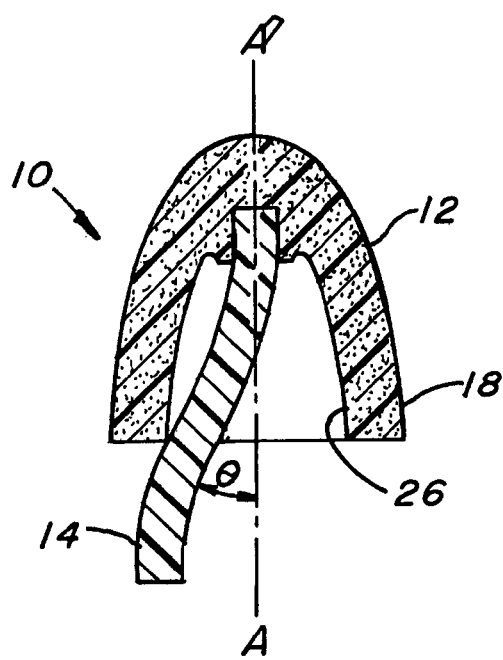
Figure 25:
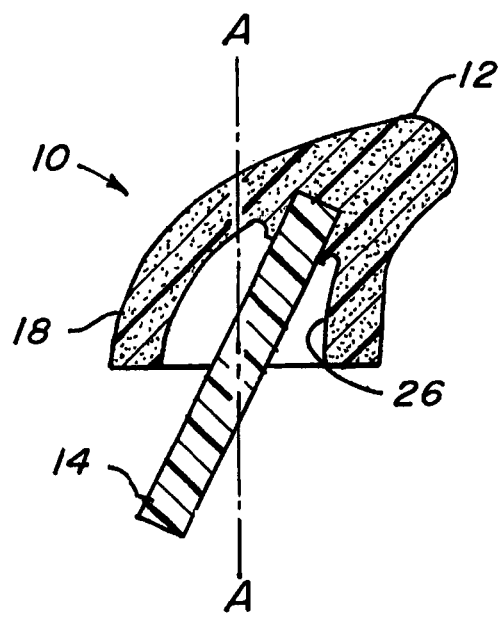

However, this description of the disposition of the stem 14 is by no means limiting on the scope of the invention. For example, referring to FIG. 23, the stem portion 14 may be disposed at an angle θ with respect to the longitudinal axis A-A of the earplug 10. This angle θ may generally range from 0-60°. More preferably, the angle θ is approximately 0-30°. In this embodiment, the angled stem portion 14 is a straight element as shown in FIG. 23 or may include any type of curving or contouring as desired. FIG. 24 shows such curved stem portion 14 extending generally at the angle θ relative to the longitudinal axis A-A of the earplug 10. It is noted that the angled stem portion 14 discussed herein with reference to FIGS. 23 and 24 extends from the earplug 10 as shown such that the stem 14 passes from the interior 26 of the sound attenuating portion 12 at a point between the longitudinal axis A-A and an outer circumference of the attenuation portion 12 formed by the flared portion 18. That is, here the stem portion 14 is not centered within the flared portion 18 upon extending therefrom to an exterior of the earplug 10. However, in another embodiment as shown in FIG. 25, the sound attenuating portion 12 may be skewed to one side of the axis A-A such that the stem portion 14 exits the interior 26 of the sound attenuating portion 12 at a point substantially intersecting the axis A-A at a center of the flared portion 18. The stem 14 of FIG. 25 may, of course, be curved or contoured as desired. These and any additional configurations and dispositions of the stem portion 14 which are suitable for facilitating insertion, retention, occlusion, and removal of the earplug 10 relative to the ear canal, are contemplated by the invention.

As mentioned hereinabove, the interior 26 of the earplug of the invention, in its various embodiments, may have various lengths in relation to the longitudinal length of the respective sound attenuating portion 12. Put another way, the depth of the interior 26 of the earplug may be configured as desired so as to be relatively deep (see, e.g., FIGS. 17-19 and 22-25) or relative shallow (see, e.g., FIGS. 21, 29, and 30).

Such a shallow configuration is shown, for example, in FIGS. 29-30. Therein, an earplug 200 is shown in accordance with this invention as including the sound attenuating portion 12 having the bulbous portion 16 at the front insertion end, the flared portion 18 at the rear end, and the body portion 20 extending therebetween. The depth or length of the interior 26 of the earplug 200 is relatively less than the overall longitudinal length of the sound attenuating portion 12 and, more specifically, is relatively less than half of the longitudinal length of the sound attenuating portion 12. That is, here the interior 26 forms a shallow recess at the rear end of the earplug 200. However, the sound attenuating portion 12 (particularly the part thereof extending about the interior 26) is still permitted to collapse inwardly towards the interior when the earplug 200 is inserted into an ear canal, thus providing enhanced comfort, fit, and attenuation as discussed hereinabove with respect to the various embodiments of the invention. The earplug 200 is shown here without a stem portion. The earplug 200, along with the other various exemplary earplug embodiments described herein, may be used with or without a stem portion, as desired. In using the earplug 200 as shown, without a stem portion, the user simply grasps the rear end of the earplug proximate to the flared portion 18 and inserts the earplug, insertion end first, into the ear canal as generally described herein. Of course, the earplug 200 may be compressed or 'rolled-down' prior to insertion. Alternatively, the earplug 200 may be equipped with the stem portion 14 by processes and methods described hereinabove with respect to other various embodiments of the invention.

Figure 26:
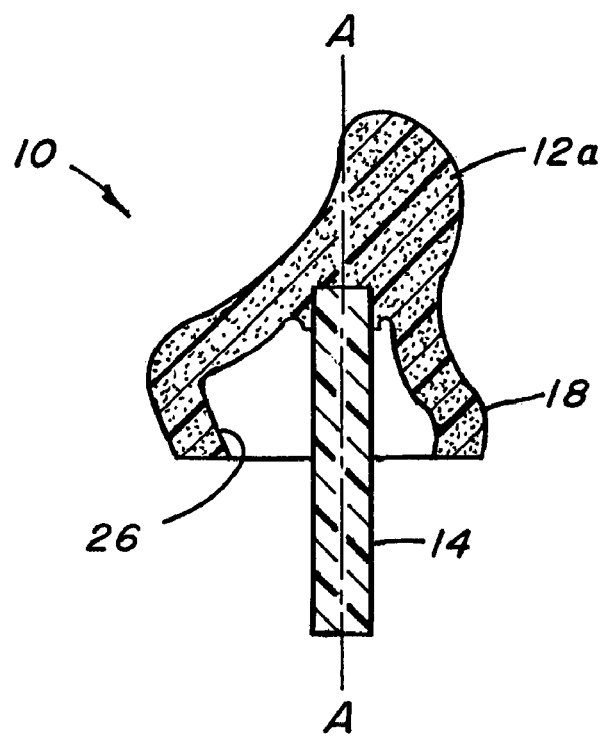
Figure 27:
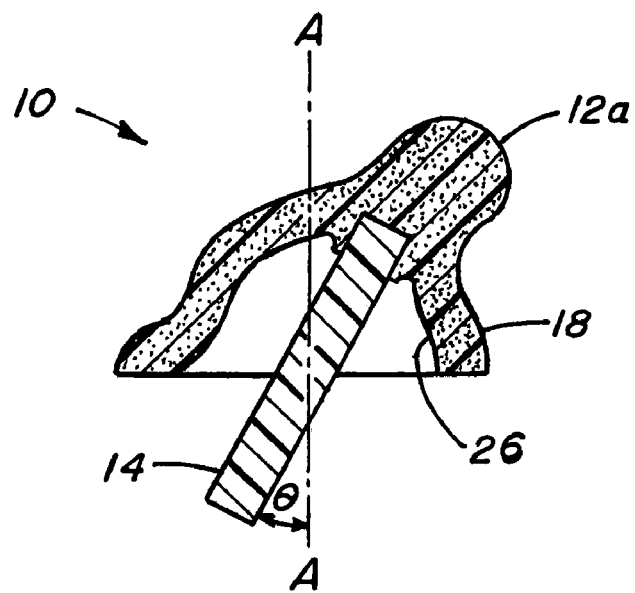
Figure 28:
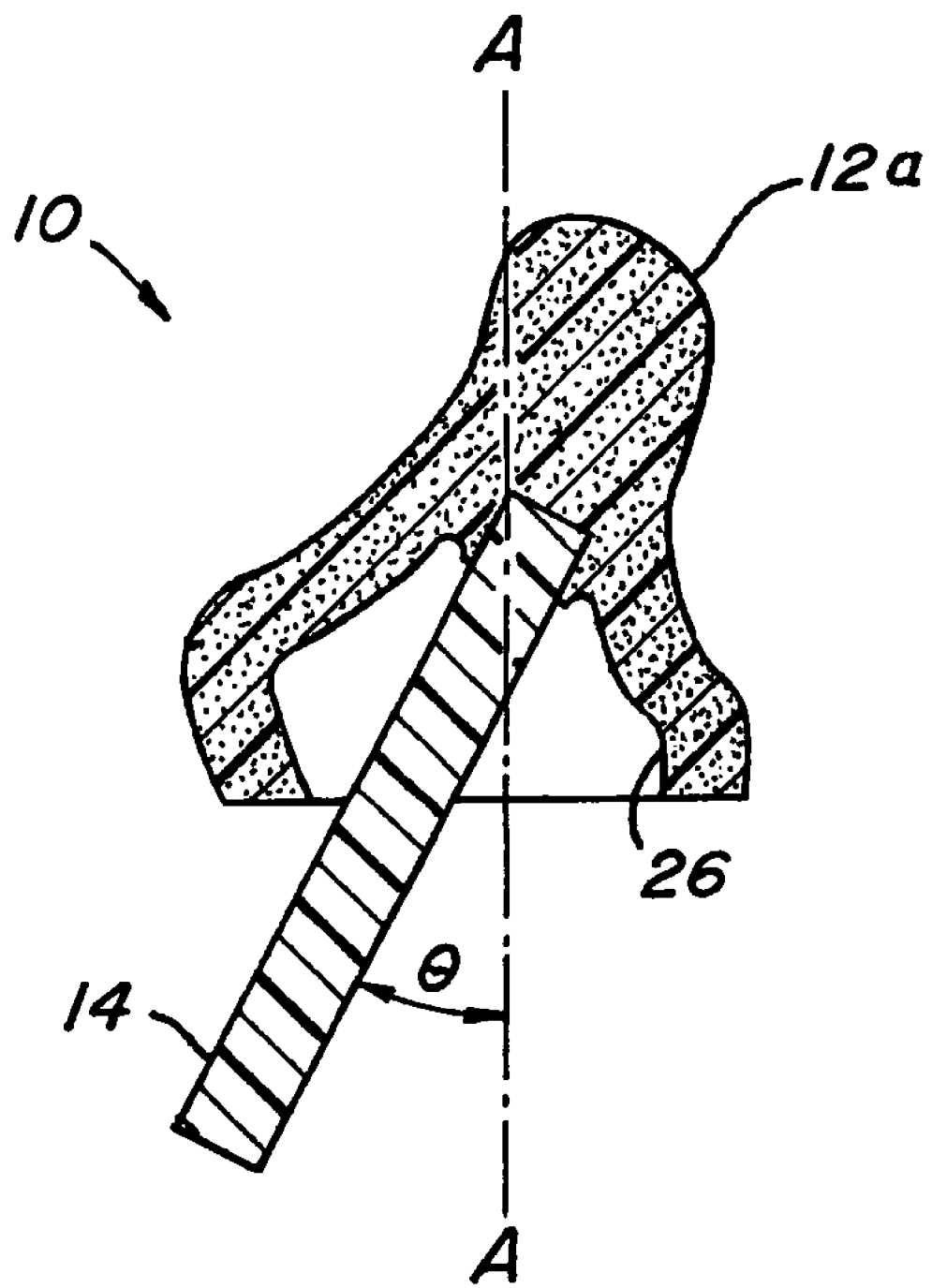

The sound attenuating portion 12 of the earplug 10 is described herein as including any desired shape and is preferably 'bell-shaped' as shown in FIG. 1. Various exemplary additional shapes of the attenuating portion 12 are shown in FIGS. 17-21 and described in the corresponding text. Additionally, it is noted that the sound attenuating portion may include irregularities or various contouring, as desired. Such a contoured sound attenuating element 12a is shown in one embodiment in FIGS. 26-28. Therein, the sound attenuating element 12a includes contouring comprising curvilinear surface features as shown. FIG. 26 depicts the earplug 10 including the contoured sound attenuating portion 12a and the stem portion 14 extending therefrom aligned with the axis A-A. FIGS. 27 and 28 show the earplug 10 with the contoured sound attenuating portion 12a having the stem portion 14 extending therefrom at the angle θ to the axis A-A. The angle θ is between approximately 0-60° and preferably between approximately 0-30°. In FIG. 27, the stem portion 14 extends from the interior 26 of the sound attenuating portion 12 through a center of the flared portion 18 generally indicated by the intersection of flared portion 18 and the axis A-A. In FIG. 28, the stem 14 extends through the flared portion 18 at a point between its outer circumference and the axis A-A. Here again, the stem portion 14 of course may include any curving or contouring as desired. These and other configurations of the contoured/irregular shaped sound attenuating portion 12a and the disposition and configuration of the stem 14 disposed there, are contemplated by the invention In an example of the invention, an earplug according to the description set forth herein was tested using conventional procedures against a frequency range of 125-8000 Hz. Specifically, the earplug was tested according to industry standard procedures set forth at ANSI S319-1974. That is, ten individuals were tested three times each across the indicated range of frequencies. The test results indicated an NRR of the earplug of 30 dB, well exceeding attenuation provided by known push-in type earplugs.

Thus, the invention clearly provides a hearing protection device which is inserted within the ear canal in a simple and effective manner, which stays firmly in place therein after insertion even during periods of extended or rigorous usage, which provides enhanced comfort to the user, and which provides a relatively high sound attenuation for a push-in type hearing protector.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A hearing protection device insertable into an earcanal, comprising:
    a stem portion;
    a sound attenuating portion affixed to the stem portion and including:
        a sleeve for receiving and retaining the stem, and
        a single flange extending over and beyond the sleeve and extending at least partially over the stem portion; and
    a continuous, unobstructed volume of space disposed between and delimited by the single flange, the sleeve, and the stem portion;
    wherein the sound attenuating portion extends at least approximately half of a length of the hearing protection device and less than approximately an entire length of the hearing protection device;
    wherein the single flange extends approximately half of the length of the sound attenuating portion; and
    wherein the single flange is fully collapsible into the volume of space during insertion of the hearing protection device into the ear canal.

2. The hearing protection device of claim 1, wherein the stem portion includes a front portion which is inserted and retained within the sound attenuating portion at the sleeve and an opposite rear portion which extends from the sound attenuating portion and the sleeve through the volume of space.

3. The hearing protection device of claim 2, wherein the front of the stem portion is affixed to the sound attenuating portion at the sleeve by an adhesive agent.

4. The hearing protection device of claim 2, wherein the rear of the stem portion extends from the sound attenuating portion, through the volume of space, and includes features for facilitating handling of the device.

5. The hearing protection device of claim 4, wherein the features comprise at least one of a projection and a recess formed in an outer surface of the stem portion.

6. The hearing protection device of claim 2, further comprising a cavity formed in the stem portion along a longitudinal axis thereof for receiving and retaining a cord, the cavity including an opening at the rear portion of the stem.

7. The hearing protection device of claim 1, further comprising a bulbous portion disposed at a front of the sound attenuating portion.

8. The hearing protection device of claim 7, wherein the bulbous portion includes a partially spherical shape.

9. The hearing protection device of claim 1, further comprising a flared portion disposed at a rear of the sound attenuating portion.

10. The hearing protection device of claim 9, wherein the flared portion comprises an annular shaped element which extends in a smooth curve outwardly from a longitudinal axis of the device.

11. The hearing protection device of claim 1, wherein the sound attenuating portion includes a substantially circular cross-section which varies in area from the front to the rear thereof such that the sound attenuating portion includes a smallest cross-section at a front end and a largest cross-section at the rear end.

12. The hearing protection device of claim 1, wherein the sound attenuating portion is substantially bell-shaped and includes a partially spherical bulbous portion at a front end and a flared portion at a rear end, the flared end extending outwardly from a longitudinal axis of the sound attenuating portion.

13. The hearing protection device of claim 12, wherein the single elongated flange element extends between the bulbous portion and the flared portion, the elongated flange element including a plurality of concentric rings on an outer surface thereof of serially increasing diameters from the front to the rear of the sound attenuating portion.

14. The hearing protection device of claim 13, wherein the rings form a plurality of corresponding steps along a profile of the sound attenuating portion.

15. The hearing protection device of claim 1, further comprising a plurality of concentric circular ridges formed about the sound attenuating portion between a front end and an opposing rear end to facilitate handling of the device and retention of the device within the ear canal.

16. The hearing protection device of claim 1, wherein the sleeve extends into the volume of space along a longitudinal axis of the sound attenuating portion toward a rear thereof and includes a cavity for receiving the stem portion.

17. The hearing protection device of claim 16, further comprising a plurality of ribs disposed on the sound attenuating portion at the interior thereof extending from the sleeve to the rear of the sound attenuating portion.

18. The hearing protection device of claim 17, wherein the ribs taper in cross-sectional area in a direction toward the rear of the sound attenuating portion.

19. The hearing protection device of claim 17, wherein the plurality of ribs comprises four ribs equally spaced about an interior surface of the sound attenuating portion.

20. The hearing protection device of claim 1, wherein the sound attenuating portion is composed of a foam material having a Shore OO durometer of approximately 20 to 40.

21. The hearing protection device of claim 1, wherein the sound attenuating portion is composed of a foam material having a Shore OO durometer of approximately 30.

22. The hearing protection device of claim 20, wherein the stem portion is formed of a material having a Shore A durometer of approximately 60 to 100.

23. The hearing protection device of claim 22, wherein the stem portion is formed of a material having a Shore A durometer of approximately 80.

24. The hearing protection device of claim 1, wherein the volume of space is substantially frustoconical in shape.

25. The hearing protection device of claim 1, wherein the sound attenuating portion is formed a compressible resilient material.

26. The hearing protection device of claim 25, wherein the compressible resilient material is a foam.

27. The hearing protection device of claim 26, wherein the foam comprises at least one of a polyurethane, an acrylic blend, a PVC, a silicone, and a nitrile foam.

28. The hearing protection device of claim 25, wherein the compressible resilient material is a plastic or a rubber material or a composition thereof.

29. The hearing protection device of claim 28, wherein the compressible resilient material is a thermoplastic elastomer.

30. The hearing protection device of claim 1, wherein the sound attenuating portion includes a rounded front end.

31. The hearing protection device of claim 30, wherein the sound attenuating portion includes a substantially cylindrical shape.

32. The hearing protection device of claim 30, wherein the sound attenuating portion includes a partially spherical shape.

33. The hearing protection device of claim 1, wherein the sound attenuating portion includes a single flange extending over the stem toward a rear of the device to form the volume of space, the flange collapsible into the space.

34. The hearing protection device of claim 1, wherein the front of the stem portion is affixed to the sound attenuating portion at the sleeve by a chemical bonding.

35. The device of claim 1, wherein the stem portion extends from the volume of space to an exterior of the device at an angle of approximately 0-60° related to a longitudinal axis of the earplug.

36. The device of claim 35, wherein the angle is approximately 0-30°.

37. The device of claim 35, wherein the stem portion is an elongated curved element.

38. The device of claim 35 wherein, the sound attenuating portion includes an opening to the exterior of the device, the stem portion extending from the device through a center of the opening.

39. The device of claim 35 wherein, the sound attenuating portion includes an opening to the exterior of the device, the stem portion extending from the device through the opening between a center of the opening and an outer edge of the opening.

40. The device of claim 35, wherein the sound attenuation portion includes an irregular shape.

41. The device of claim 1, wherein the sound attenuation portion includes an irregular shape.

42. The hearing protection device of claim 1, wherein the single elongated flange element that includes a plurality of concentric rings on an outer surface thereof, the rings being of serially increasing diameters from a front to a rear of the sound attenuating portion.

43. The hearing protection device of claim 42, wherein the rings form a plurality of corresponding steps along a profile of the sound attenuating portion.

44. A hearing protection device insertable into an ear canal, comprising:

a stem portion having a front end and an opposite rear end;

a single flange element fixed to the front end of the stem portion and extending over at least a portion of the stem portion toward the rear of the stem portion, said flange element extending at least approximately half of a length of the hearing protection device and less than approximately an entire length of the hearing protection device;

a sleeve configured to receive and retain the stem portion, the sleeve extending at least partially over the stem portion, the single flange disposed to extend over and beyond the sleeve;

a volume of space delimited by the stem portion, the sleeve, and the single flange element;

wherein the flange element is formed of a compressible resilient material and the flange element is fully collapsible into the volume of space during insertion of the earplug into the ear canal.

45. The hearing protection device of claim 44, wherein the single flange element includes an elongated conical shape and is composed of a foam having a Shore OO durometer of approximately 20 to 40.

46. A sound attenuating portion of a hearing protection device, the sound attenuating portion being configured for insertion into an ear canal, comprising:

a front insertable portion formed of a compressible resilient material;

a flange portion extending rearwardly from the front insertable portion and a volume of space formed at an interior of the flange portion rearward of the front insertable portion;

wherein the flange portion extends out of contact from a remainder of the hearing protection device and at least approximately half of a length of the sound attenuating portion and less than approximately an entire length of the hearing protection device, and wherein the flange portion is fully collapsible into the volume of space.

47. The device-portion of claim 46, further comprising a bulbous portion at a front end thereof.

48. The portion of claim 47, further comprising a flared portion at a rear end thereof extending outwardly from a longitudinal axis of the device.

49. The portion of claim 48, wherein the bulbous portion includes a partially spherical shape and the flared portion is formed of a smooth curve extending from a body portion of the device outwardly from the longitudinal axis.

50. The portion of claim 46, further comprising a substantially circular cross-section which varies in area from a front to a rear thereof such that the portion includes a smallest cross-section at a front end and a largest cross-section at the rear end.

51. The portion of claim 46, wherein the sound attenuating portion is substantially bell-shaped and includes a partially spherical bulbous portion at a front end and a flared portion at a rear end, the flared end extending outwardly from a longitudinal axis of the sound attenuating portion.

52. The portion of claim 46, further comprising a plurality of concentric circular ridges formed about the portion between a front end and an opposing rear end to facilitate handling of the portion and retention of the portion within the ear canal.

53. The hearing protection portion of claim 46, wherein the sound attenuating portion is formed a compressible resilient material.

54. The hearing protection portion of claim 53 wherein the compressible resilient material is at least one of a polyurethane, an acrylic blend, a PVC, a silicone, and a nitrile foam.

55. The hearing protection portion of claim 53, wherein the compressible resilient material is a plastic or a rubber material or a composition thereof.

56. The portion of claim 46, further comprising a shape of at least one of frustoconical, conical, partially spherical, and cylindrical.

57. The portion of claim 46 wherein the volume of space is substantially conical in shape.

58. The device of claim 46, wherein the compressible resilient material comprises a foam and wherein the volume of space formed thereby is partially spherical in shape.

59. The device of claim 46, wherein a length of a part of the flange portion which extends over the volume of space is approximately less than half of an overall longitudinal length of the flange portion.

60. The device of claim 46, wherein a length of a part of the flange portion which extends over the volume of space is approximately less than one-quarter of an overall longitudinal length of the flange portion.

* * * * *

UNITED STATES PATENT AND TRADEMARK OFFICE
CERTIFICATE OF CORRECTION

PATENT NO. : 7,464,786 B2  
APPLICATION NO. : 10/866212  
DATED : December 16, 2008  
INVENTOR(S) : Robert N. Falco Page 1 of 1

It is certified that error appears in the above-identified patent and that said Letters Patent is hereby corrected as shown below:

Column 6
Line 25, before "one" delete "in" and insert -- In --, therefor.
Line 30, delete "gradually." and insert -- gradually --, therefor.

Column 14
Line 39, in claim 35, delete "related" and insert -- relative --, therefor.

Signed and Sealed this

Nineteenth Day of May, 2009

JOHN DOLL
*Acting Director of the United States Patent and Trademark Office*